(12) United States Patent
Stoessel et al.

(10) Patent No.: US 8,637,168 B2
(45) Date of Patent: Jan. 28, 2014

(54) MATERIALS FOR ORGANIC ELECTROLUMINESCENCE DEVICES

(75) Inventors: Philipp Stoessel, Frankfurt (DE); Holger Heil, Frankfurt (DE); Dominik Joosten, Frankfurt (DE); Christof Pflumm, Frankfurt (DE); Anja Gerhard, Egelsbach (DE)

(73) Assignee: Merck Patent GmbH, Darmstadt (DE)

( * ) Notice: Subject to any disclaimer, the term of this patent is extended or adjusted under 35 U.S.C. 154(b) by 364 days.

(21) Appl. No.: 13/001,887

(22) PCT Filed: Sep. 10, 2009

(86) PCT No.: PCT/EP2009/006556
§ 371 (c)(1),
(2), (4) Date: Dec. 29, 2010

(87) PCT Pub. No.: WO2010/040438
PCT Pub. Date: Apr. 15, 2010

(65) Prior Publication Data
US 2011/0108823 A1    May 12, 2011

(30) Foreign Application Priority Data

Oct. 8, 2008 (DE) .......................... 10 2008 050 841

(51) Int. Cl.
*H01L 51/52* (2006.01)
*C07C 211/54* (2006.01)
*C07D 401/00* (2006.01)
*C07D 401/12* (2006.01)
*C09K 11/06* (2006.01)

(52) U.S. Cl.
USPC ............. 428/690; 428/917; 257/40; 564/307; 564/434; 548/444; 252/301.16; 313/504; 313/506

(58) Field of Classification Search
None
See application file for complete search history.

(56) References Cited

U.S. PATENT DOCUMENTS

| 4,539,507 | A | 9/1985 | VanSlyke et al. |
| 5,151,629 | A | 9/1992 | VanSlyke |
| 5,621,131 | A | 4/1997 | Kreuder et al. |
| 5,840,217 | A | 11/1998 | Lupo et al. |
| 6,458,909 | B1 | 10/2002 | Spreitzer et al. |
| 6,653,438 | B1 | 11/2003 | Spreitzer et al. |
| 6,908,783 | B1 | 6/2005 | Kuehl et al. |
| 7,345,301 | B2 | 3/2008 | Gerhard et al. |
| 7,659,540 | B2 | 2/2010 | Heun et al. |
| 7,701,131 | B2 | 4/2010 | Gerhard et al. |
| 7,723,455 | B2 | 5/2010 | Becker et al. |
| 7,795,801 | B2 | 9/2010 | Ueda et al. |
| 7,799,875 | B2 | 9/2010 | Buesing et al. |
| 7,820,305 | B2 | 10/2010 | Schulte et al. |
| 7,820,822 | B2 | 10/2010 | Fortte et al. |
| 7,834,136 | B2 | 11/2010 | Parham et al. |
| 7,858,967 | B2 | 12/2010 | Pfeiffer et al. |
| 2004/0062947 | A1* | 4/2004 | Lamansky et al. ............ 428/690 |
| 2004/0151944 | A1 | 8/2004 | Onikubo et al. |
| 2005/0040390 | A1 | 2/2005 | Pfeiffer et al. |
| 2005/0069729 | A1 | 3/2005 | Ueda et al. |
| 2005/0121667 | A1 | 6/2005 | Kuehl et al. |
| 2006/0149022 | A1 | 7/2006 | Parham et al. |
| 2006/0175958 | A1 | 8/2006 | Gerhard et al. |
| 2006/0208221 | A1 | 9/2006 | Gerhard et al. |
| 2006/0251925 | A1* | 11/2006 | Hosokawa et al. ........... 428/690 |
| 2006/0255332 | A1 | 11/2006 | Becker et al. |
| 2006/0284140 | A1 | 12/2006 | Breuning et al. |
| 2007/0034863 | A1 | 2/2007 | Fortte et al. |
| 2007/0060736 | A1 | 3/2007 | Becker et al. |
| 2007/0080343 | A1 | 4/2007 | Heun et al. |
| 2007/0176147 | A1 | 8/2007 | Buesing et al. |
| 2007/0205714 | A1 | 9/2007 | Busing et al. |
| 2007/0281182 | A1 | 12/2007 | Schulte et al. |
| 2008/0125609 | A1 | 5/2008 | Vestweber et al. |
| 2008/0145698 | A1 | 6/2008 | Heil et al. |
| 2008/0220285 | A1 | 9/2008 | Vestweber et al. |
| 2008/0272693 | A1 | 11/2008 | Heil et al. |
| 2009/0005505 | A1 | 1/2009 | Buesing et al. |
| 2009/0058289 | A1 | 3/2009 | Stoessel et al. |
| 2009/0134384 | A1 | 5/2009 | Stoessel et al. |
| 2009/0159874 | A1 | 6/2009 | Vestweber et al. |
| 2009/0167166 | A1 | 7/2009 | Bach et al. |
| 2009/0184313 | A1 | 7/2009 | Buesing et al. |
| 2009/0226759 | A1 | 9/2009 | Heun et al. |
| 2009/0261717 | A1 | 10/2009 | Buesing et al. |
| 2009/0302742 | A1 | 12/2009 | Komori et al. |
| 2009/0302752 | A1 | 12/2009 | Parham et al. |

(Continued)

FOREIGN PATENT DOCUMENTS

EP    652273 A1    5/1995
EP    676461 A2    10/1995

(Continued)

OTHER PUBLICATIONS

Translation for JP 2007-291037, published Nov. 2007 (Printed as Part 1 and Part 2).*

(Continued)

*Primary Examiner* — Dawn L. Garrett
(74) *Attorney, Agent, or Firm* — Novak Druce Connolly Bove + Quigg LLP

(57) ABSTRACT

The present invention relates to aromatic amines and to electronic devices in which these amines are used, in particular, as matrix material in the emitting layer and/or as hole-transport material and/or as electron-blocking or exciton-blocking material and/or as electron-transport material.

18 Claims, No Drawings

(56) References Cited

U.S. PATENT DOCUMENTS

| | | |
|---|---|---|
| 2010/0102305 A1 | 4/2010 | Heun et al. |
| 2010/0187977 A1 | 7/2010 | Kai et al. |
| 2010/0288974 A1 | 11/2010 | Buesing et al. |
| 2010/0331506 A1 | 12/2010 | Fortte et al. |
| 2011/0068304 A1 | 3/2011 | Parham et al. |

FOREIGN PATENT DOCUMENTS

| | | |
|---|---|---|
| EP | 707020 A2 | 4/1996 |
| EP | 842208 A1 | 5/1998 |
| EP | 894107 A1 | 2/1999 |
| EP | 1028136 A2 | 8/2000 |
| EP | 1191612 A2 | 3/2002 |
| EP | 1191613 A2 | 3/2002 |
| EP | 1191614 A2 | 3/2002 |
| EP | 1205527 A1 | 5/2002 |
| EP | 1476881 A2 | 11/2004 |
| EP | 1596445 A1 | 11/2005 |
| EP | 1617710 A1 | 1/2006 |
| EP | 1617711 A1 | 1/2006 |
| EP | 1731584 A1 | 12/2006 |
| JP | 3171755 A | 7/1991 |
| JP | 09-148072 A | 6/1997 |
| JP | 2004-288381 A | 10/2004 |
| JP | 2005-347160 A | 12/2005 |
| JP | 2007-291037 A | 11/2007 |
| JP | 2008-056625 A | 3/2008 |
| WO | WO-92/18552 A1 | 10/1992 |
| WO | WO-97/05184 A1 | 2/1997 |
| WO | WO-97/39045 A1 | 10/1997 |
| WO | WO-98/27136 A1 | 6/1998 |
| WO | WO-00/22026 A1 | 4/2000 |
| WO | WO-00/70655 A2 | 11/2000 |
| WO | WO-01/41512 A1 | 6/2001 |
| WO | WO-02/02714 A2 | 1/2002 |
| WO | WO-02/15645 A1 | 2/2002 |
| WO | WO-03070822 A2 | 8/2003 |
| WO | WO-2004/041901 A1 | 5/2004 |
| WO | WO-2004/070772 A2 | 8/2004 |
| WO | WO-2004/093207 A2 | 10/2004 |
| WO | WO-2004/113412 A2 | 12/2004 |
| WO | WO-2004/113468 A1 | 12/2004 |
| WO | WO-2005/003253 A2 | 1/2005 |
| WO | WO-2005/011013 A1 | 2/2005 |
| WO | WO-2005/014689 A2 | 2/2005 |
| WO | WO-2005/033244 A1 | 4/2005 |
| WO | WO-2005/039246 A1 | 4/2005 |
| WO | WO-2005/040302 A1 | 5/2005 |
| WO | WO-2005/104264 A1 | 11/2005 |
| WO | WO-2005/111172 A2 | 11/2005 |
| WO | WO-2006/000388 A1 | 1/2006 |
| WO | WO-2006/000389 A1 | 1/2006 |
| WO | WO-2006003000 A1 | 1/2006 |
| WO | WO-2006/058737 A1 | 6/2006 |
| WO | WO-2006/061181 A1 | 6/2006 |
| WO | WO-2006/117052 A1 | 11/2006 |
| WO | WO-2006/122630 A1 | 11/2006 |
| WO | WO-2007/017066 A1 | 2/2007 |
| WO | WO-2007/063754 A1 | 6/2007 |
| WO | WO-2007/065549 A1 | 6/2007 |
| WO | WO-2007068325 A1 | 6/2007 |
| WO | WO-2007115610 A1 | 10/2007 |
| WO | WO-2007/137725 A1 | 12/2007 |
| WO | WO-2007/140847 A1 | 12/2007 |
| WO | WO-2008/006449 A1 | 1/2008 |
| WO | WO-2008/056746 A1 | 5/2008 |
| WO | WO-2008/086851 A1 | 7/2008 |

OTHER PUBLICATIONS

Translation for JP 2008-056625, published Mar. 2008 (Printed as Part 1 and Part 2).*
Translation for JP 09-148072, published Jun. 1997.*

* cited by examiner

MATERIALS FOR ORGANIC ELECTROLUMINESCENCE DEVICES

RELATED APPLICATIONS

This application is a national stage application (under 35 U.S.C. §371) of PCT/EP2009/006556, filed Sep. 10, 2009, which claims benefit of German Application No. 10 2008 050 841.1, filed Oct. 8, 2008.

The present invention relates to organic semiconductors and to the use thereof in electronic devices.

Organic semiconductors are being developed for a number of electronic applications of different types. The structure of organic electroluminescent devices (OLEDs) in which these organic semiconductors are employed as functional materials is described, for example, in U.S. Pat. No. 4,539,507, U.S. Pat. No. 5,151,629, EP 0676461 and WO 98/27136. However, further improvements are still necessary. For example, there is still a need for improvement, in particular, in the lifetime and the efficiency of blue-emitting organic electroluminescent devices. It is furthermore necessary for the compounds to have high thermal stability and a high glass-transition temperature and to be sublimable without decomposition. In particular for use at elevated temperature, a high glass-transition temperature is essential for achieving long lifetimes.

There continues to be a demand for improved materials, for example host materials for fluorescent and phosphorescent emitters, but, in particular, also for charge-transport materials, i.e. hole- and electron-transport materials, and charge-blocking materials. In particular, the properties of these materials are frequently responsible for the short lifetime and low efficiency of the organic electroluminescent device.

Surprisingly, it has been found that ortho-diarylamine-substituted aromatic compounds have particularly good charge-transport properties and in addition crucially improve the efficiency and lifetime of the electronic devices produced therewith.

In particular, it has been found that aromatic compounds which are ortho-substituted by diarylamine derivatives are very highly suitable for use in organic electroluminescent devices, where they result in significant improvements compared with the prior art. This likewise applies if the compound is substituted by further substituents or if corresponding heterocyclic derivatives are used. The present invention therefore relates to these compounds and to the use thereof in electronic devices. Depending on the substitution, the compounds according to the invention are particularly suitable as hole-transport materials, electron- or exciton-blocking materials or matrix materials for fluorescent or phosphorescent compounds, but can also be employed as hole-blocking materials and electron-transport materials. With the materials according to the invention, an increase in the efficiency with the same or an improved lifetime of the organic electronic device is possible compared with materials in accordance with the prior art. Furthermore, these compounds have high thermal stability. In general, these materials are very highly suitable for use in electronic devices since they have a high glass-transition temperature.

Prior art which may be mentioned comprises the specifications US 2004/0151944 A1 and JP 2008/056625 A.

US 2004/0151944 A1 discloses a red- or orange-fluorescent dopant/matrix mixture, where the host has a perylene structure and the red dopant has a diketopyrrolopyrrole structure. However, the host structures are not suitable for also encompassing the colours green and blue. In addition, there is still a need for improvement in the case of use in a charge-transport or charge-injection layer.

JP 2008/056625 A uses ortho-diarylamine-substituted naphthalenes in hole-transport layers. However, there is still a need for improvement with respect to the stability and lifetime. In addition, these compounds are not suitable for use in blue-phosphorescent OLEDs.

JP 3171755 B2 and JP 09-148072 A disclose ortho-substituted diarylamines. However, there is still a need for improvement with respect to the lifetime.

The invention thus relates to compounds of the formula (1)

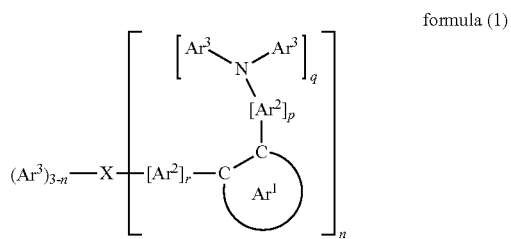

formula (1)

where the following applies to the symbols and indices used:

X is on each occurrence, identically or differently, N, P, P=O, P=S, B, 1,3,5-triazine, $N(Ar^3)_3$;

$Ar^1$ is on each occurrence, identically or differently, a group which, together with the group C—C, forms an aryl or heteroaryl group having 5 to 30 aromatic ring atoms and which may be substituted by one or more radicals $R^1$;

$Ar^2$ is on each occurrence, identically or differently, a divalent aryl or heteroaryl group having 5 to 30 aromatic ring atoms, which may in each case be substituted by one or more radicals $R^1$; two radicals $Ar^2$ which are bonded to the same group X may also be linked to one another by a single bond or a bridge selected from $B(R^2)$, $C(R^2)_2$, $Si(R^2)_2$, C=O, C=$NR^2$, C=$C(R^2)_2$, O, S, S=O, $SO_2$, $N(R^2)$, $P(R^2)$ and P(=O)$R^2$;

$Ar^3$ is on each occurrence, identically or differently, a monovalent aryl or heteroaryl group having 5 to 16 aromatic ring atoms, which may in each case be substituted by one or more radicals $R^1$; two radicals $Ar^3$ which are bonded to the same N may also be linked to one another by a single bond or a bridge selected from $B(R^2)$, $C(R^2)_2$, $Si(R^2)_2$, C=O, C=$NR^2$, C=$C(R^2)_2$, O, S, S=O, $SO_2$, $N(R^2)$, $P(R^2)$ and P(=O)$R^2$;

$R^1$ is on each occurrence, identically or differently, H, D, F, Cl, Br, I, CHO, C(=O)Ar, P(=O)$(Ar)_2$, S(=O)Ar, S(=O)$_2$Ar, $CR^2$=$CR^2$Ar, CN, $NO_2$, $Si(R^2)_3$, $B(OR^2)_2$, $B(R^2)_2$, $B(N(R^2)_2)_2$, $OSO_2R^2$, a straight-chain alkyl, alkoxy or thioalkoxy group having 1 to 40 C atoms or a branched or cyclic alkyl, alkoxy or thioalkoxy group having 3 to 40 C atoms or an alkenyl or alkynyl group having 2 to 40 C atoms, each of which may be substituted by one or more radicals $R^2$, where one or more non-adjacent $CH_2$ groups may be replaced by $R^2C$=$CR^2$, C≡C, $Si(R^2)_2$, $Ge(R^2)_2$, $Sn(R^2)_2$, C=O, C=S, C=Se, C=$NR^2$, P(=O)$(R^2)$, SO, $SO_2$, $NR^2$, O, S or $CONR^2$ and where one or more H atoms may be replaced by D, F, Cl, Br, I, CN or $NO_2$, or an aromatic or heteroaromatic ring system having 5 to 60 aromatic ring atoms, which may in each case be substituted by one or more radicals $R^2$, or an aryloxy or heteroaryloxy group having 5 to 60 aromatic ring atoms, which may be substituted by one or more radicals $R^2$, or a combination of these systems; two or more adjacent substituents $R^1$ here may also form a mono- or polycyclic, aliphatic or aromatic ring system with one another;

Ar is on each occurrence, identically or differently, an aromatic or heteroaromatic ring system having 5 to 30 aromatic ring atoms, which may be substituted by one or more non-aromatic radicals $R^1$;

$R^2$ is on each occurrence, identically or differently, H, D or an aliphatic, aromatic and/or heteroaromatic organic radical having 1 to 20 C atoms, in which H atoms may also be replaced by D or F, preferably a hydrocarbon; two or more adjacent substituents $R^2$ here may also form a mono- or polycyclic, aliphatic or aromatic ring system with one another;

n is 2 or 3;

p is on each occurrence, identically or differently, 0, 1 or 2;

q is 1 if p=0 and 1 or 2 if p=1;

r is on each occurrence, identically or differently, 0, 1 or 2.

The compounds of the formula (1) preferably have a glass-transition temperature $T_G$ of greater than 70° C., particularly preferably greater than 100° C., very particularly preferably greater than 110° C.

In a preferred embodiment of the invention, the compounds of the formula (1) are neutral.

As is evident from the formula (1), n=3 means that the compound carries three ortho-substituted groups on the group X or on the groups $Ar^2$ for r>0, while n=2 means that there is a further aromatic or heteroaromatic substituent $Ar^a$. $Ar^1$ is an aromatic or heteroaromatic group which is ortho-substituted. If p=0, only one diarylamine group can be bonded to $Ar^1$. If p=1 or 2, $Ar^2$ may also be substituted by up to 2 diarylamine groups.

An aryl group in the sense of this invention contains 6 to 60 C atoms; a heteroaryl group in the sense of this invention contains 2 to 60 C atoms and at least one heteroatom, with the proviso that the sum of C atoms and heteroatoms is at least 5. The heteroatoms are preferably selected from N, O and/or S. An aryl group or heteroaryl group here is taken to mean either a simple aromatic ring, i.e. benzene, or a simple heteroaromatic ring, for example pyridine, pyrimidine, thiophene, etc., or a condensed aryl or heteroaryl group, for example naphthalene, anthracene, pyrene, quinoline, isoquinoline, etc.

An aromatic ring system in the sense of this invention contains 6 to 60 C atoms in the ring system. A heteroaromatic ring system in the sense of this invention contains 2 to 60 C atoms and at least one heteroatom in the ring system, with the proviso that the sum of C atoms and heteroatoms is at least 5. The heteroatoms are preferably selected from N, O and/or S. An aromatic or heteroaromatic ring system in the sense of this invention is intended to be taken to mean a system which does not necessarily contain only aryl or heteroaryl groups, but instead in which, in addition, a plurality of aryl or heteroaryl groups may be interrupted by a short non-aromatic unit (preferably less than 10% of the atoms other than H), such as, for example, an $sp^3$-hybridised C, N or O atom. Thus, for example, systems such as 9,9'-spirobifluorene, 9,9-diarylfluorene, triarylamine, diaryl ether, stilbene, benzophenone, etc., are also intended to be taken to be aromatic ring systems in the sense of this invention. An aromatic or heteroaromatic ring system is likewise taken to mean systems in which a plurality of aryl or heteroaryl groups are linked to one another by single bonds, for example biphenyl, terphenyl or bipyridine.

For the purposes of the present invention, a $C_1$- to $C_{40}$-alkyl group, in which, in addition, individual H atoms or $CH_2$ groups may be substituted by the above-mentioned groups, is particularly preferably taken to mean the radicals methyl, ethyl, n-propyl, i-propyl, n-butyl, i-butyl, s-butyl, t-butyl, 2-methylbutyl, n-pentyl, s-pentyl, cyclopentyl, n-hexyl, cyclohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl, heptynyl or octynyl. A $C_1$- to $C_{40}$-alkoxy group is particularly preferably taken to mean methoxy, trifluoromethoxy, ethoxy, n-propoxy, i-propoxy, n-butoxy, i-butoxy, s-butoxy, t-butoxy or 2-methylbutoxy.

In a further preferred embodiment of the invention, n=3. The compounds of the formulae (2), (3) and (4) are therefore preferred embodiments of the compounds of the formula (1),

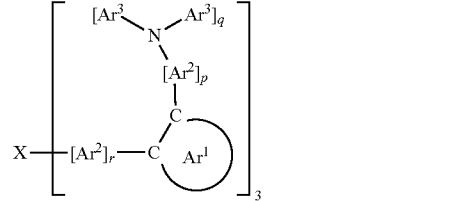

formula (2)

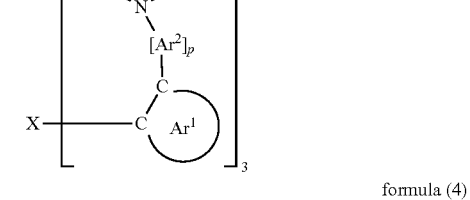

formula (3)

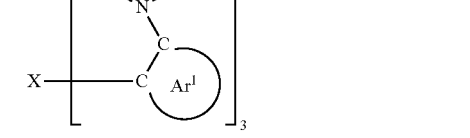

formula (4)

where the symbols and indices used have the meanings indicated above.

In a further preferred embodiment of the invention, p is equal to 0 or 1 and r is equal to 0 or 1. Particularly preferably, p=0 and r=0.

In a particularly preferred embodiment of the invention, the symbol $Ar^1$, together with the group C—C, stands for benzene, which may be substituted by one or more substituents $R^1$, in particular by one substituent $R^1$.

The substituent $R^1$ is particularly preferably in the para-position to X. In a further particularly preferred embodiment, the substituent $R^1$ is not equal to hydrogen or deuterium.

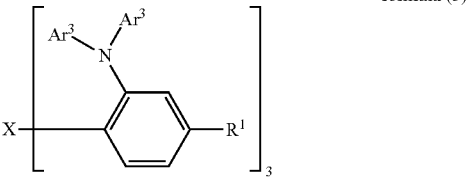

formula (5)

In a further preferred embodiment of the invention, the symbol $R^1$ in compounds of the formulae (1), (2), (3), (4) and (5) stands, identically or differently on each occurrence, for H, D, F, Br, I, CN, a straight-chain alkyl group having 1 to 10 C atoms or a branched or cyclic alkyl group having 3 to 10 C atoms, each of which may be substituted by one or more radicals $R^2$, where one or more non-adjacent $CH_2$ groups may be replaced by $R^2C=CR^2$ or O and where one or more H atoms may be replaced by D or F, or an aromatic or heteroaromatic ring system having 5 to 20 aromatic ring atoms, which may in each case be substituted by one or more radicals $R^2$, or a combination of these systems; two or more adjacent substituents $R^1$ here may also form a mono- or polycyclic, aliphatic or aromatic ring system with one another.

In a particularly preferred embodiment of the invention, the symbol $R^1$ in compounds of the formulae (1), (2), (3), (4) and (5) stands, identically or differently on each occurrence, for H, D, Br, I, CN, a straight-chain alkyl group having 1 to 6 C atoms or a branched or cyclic alkyl group having 3 to 6 C atoms, each of which may be substituted by one or more non-aromatic radicals $R^2$, where one or more H atoms may be replaced by D or F, or an aromatic or heteroaromatic ring system having 5 to 18 aromatic ring atoms, which may in each case be substituted by one or more non-aromatic radicals $R^2$; two aromatic radicals which are bonded to the same nitrogen atom may also be linked to one another by a single bond or a bridge selected from $B(R^2)$, $C(R^2)_2$, $Si(R^2)_2$, $C=O$, $C=NR^2$, $C=C(R^2)_2$, O, S, $S=O$, $SO_2$, $N(R^2)$, $P(R^2)$ and $P(=O)R^2$.

If the radical $R^1$ represents an aromatic or heteroaromatic ring system, this is preferably selected from aromatic or heteroaromatic ring systems having 5 to 30 aromatic ring atoms, in particular having 6 to 20 aromatic ring atoms, very particularly preferably from phenyl, 1-naphthyl, 2-naphthyl, anthracenyl, phenylanthracenyl, 1- or 2-naphthylanthracenyl, binaphthyl, pyrenyl, fluoranthenyl, 2-, 3-, 4-, 5-, 6- or 7-benzanthracenyl, N-benzimidazolyl, phenyl-N-benzimidazolyl, N-phenylbenzimidazolyl or phenyl-N-phenylbenzimidazolyl.

In particular, $R^1$ stands, identically or differently on each occurrence, for H, D, methyl, ethyl, isopropyl, tert-butyl or phenyl. In the case of compounds which are processed from solution, linear or branched alkyl chains having up to 10 C atoms are also preferred.

In a further preferred embodiment of the invention, $Ar^2$ in the formulae (1), (2) and (3) stands for naphthalene or benzene and may in each case be substituted by $R^1$. The symbol $Ar^2$ particularly preferably denotes benzene, which may be substituted by $R^1$.

A further preferred embodiment of the compounds of the formulae (1), (2) and (3) are molecules in which q=1, since they are particularly readily accessible synthetically.

In a further preferred embodiment, $Ar^3$ is an aromatic or heteroaromatic ring system having 5 to 10 C atoms. $Ar^3$ particularly preferably represents thiophene, phenyl or naphthalene, each of which may be substituted by one or more radicals $R^1$. The two groups $Ar^3$ here may also be connected to one another by a single bond or a divalent group, as defined above, in particular $C(R^2)_2$.

Examples of preferred compounds of the formulae (1) to (5) are structures (1) to (122) depicted below.

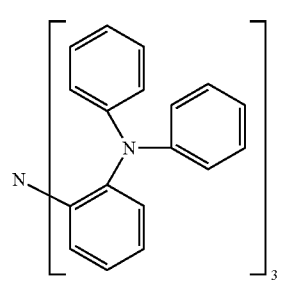

(1)

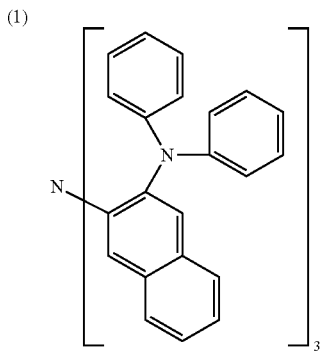

(2)

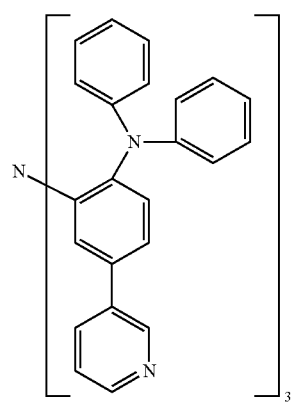

(3)

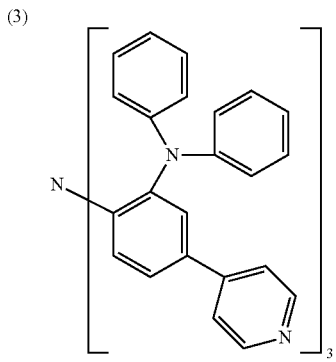

(4)

-continued
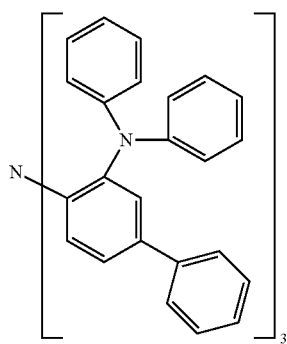
(1)
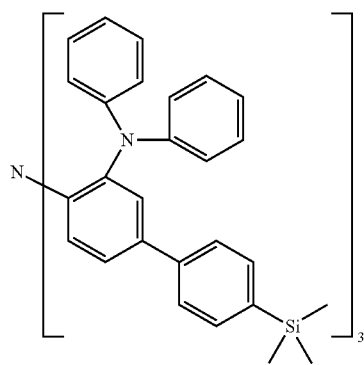
(5)
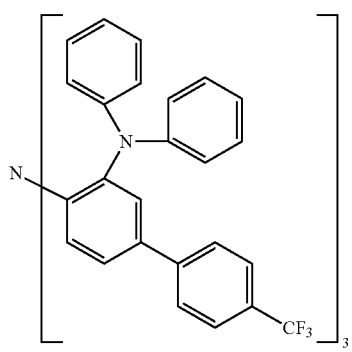
(6)
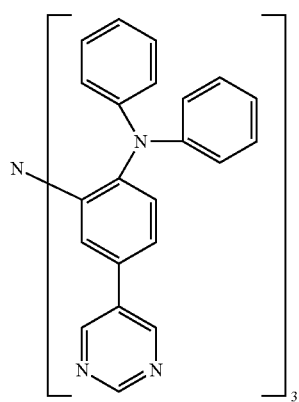
(7)
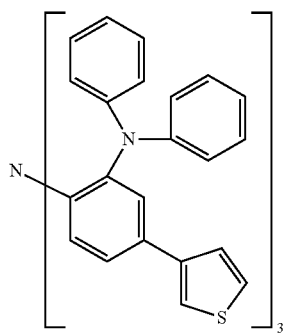
(8)
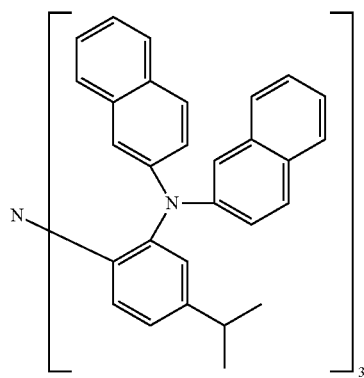
(9)
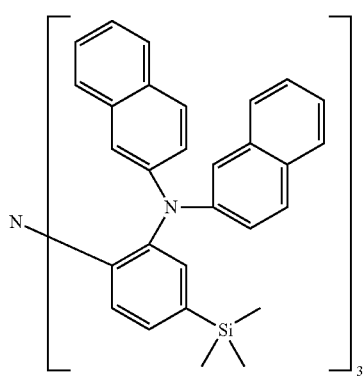
(10)
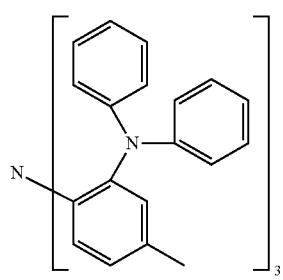
(11)
(12)

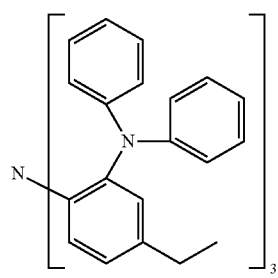
(13)
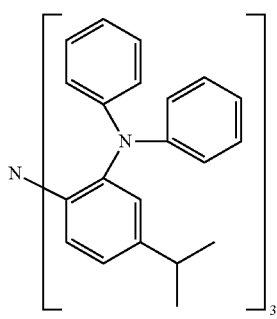
(14)
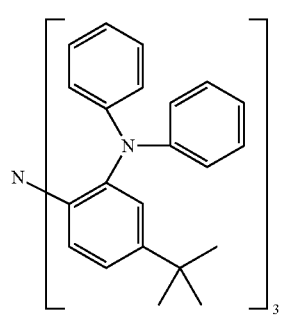
(15)
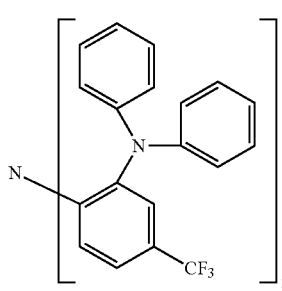
(16)
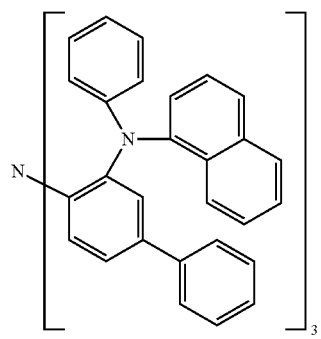
(17)
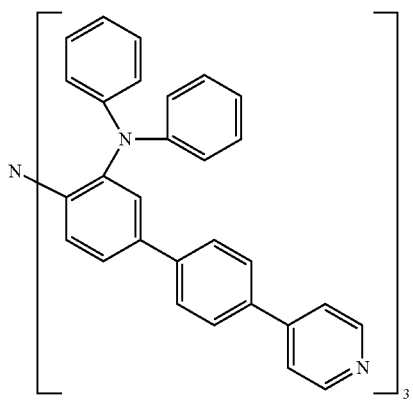
(18)
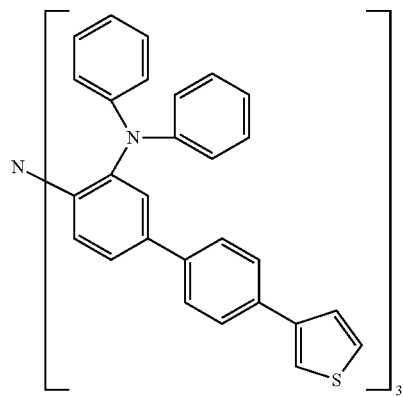
(19)
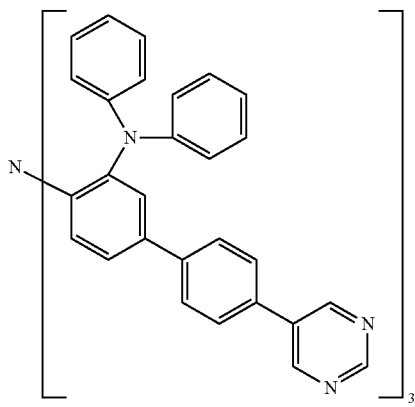
(20)

-continued
(21)
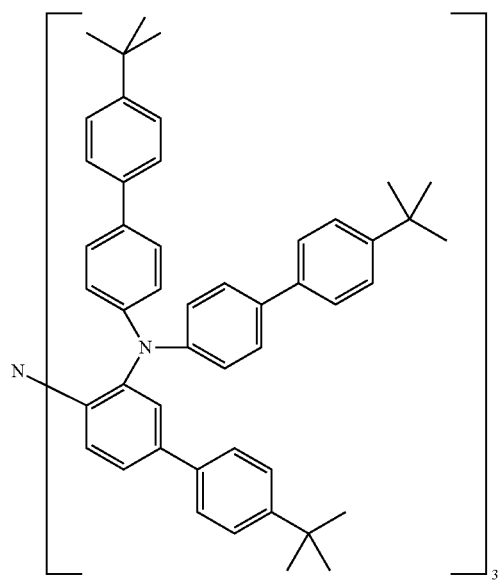
(22)
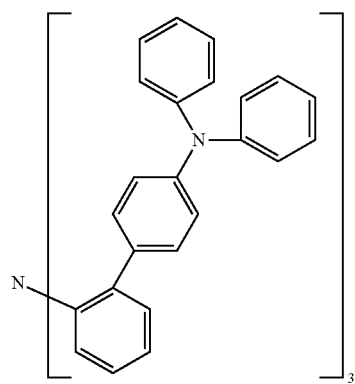
(23)
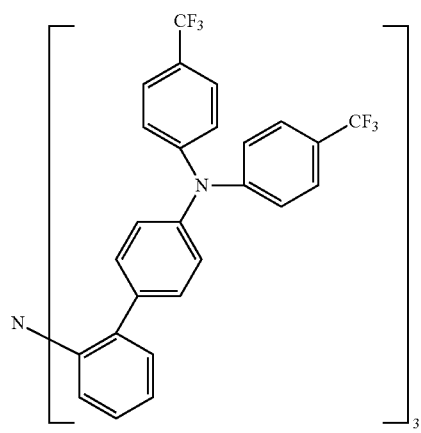
(24)
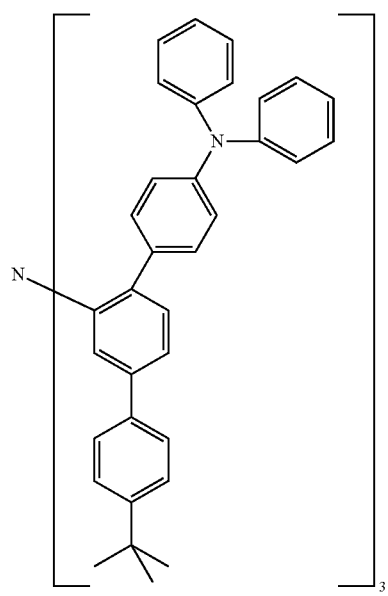

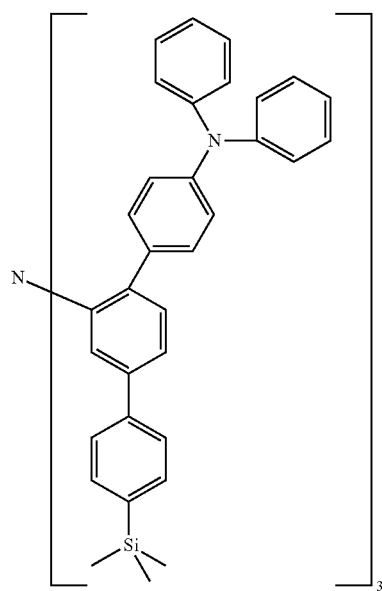
(25)
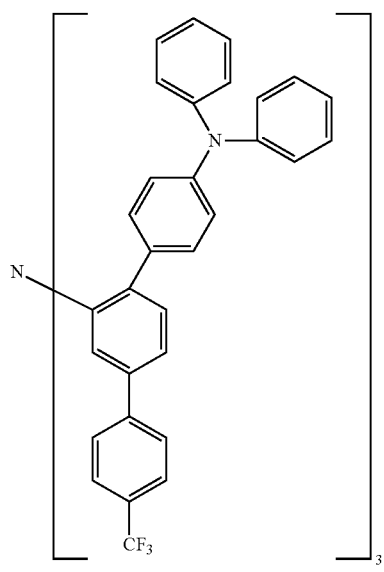
(26)
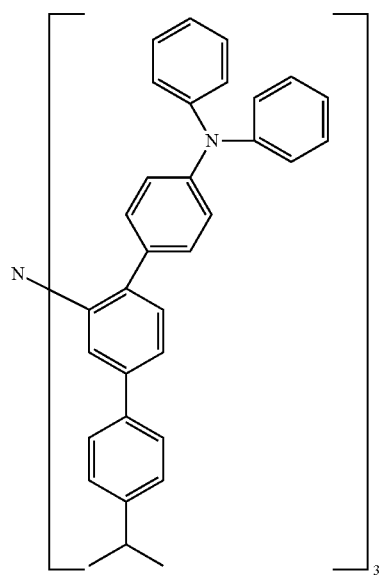
(27)
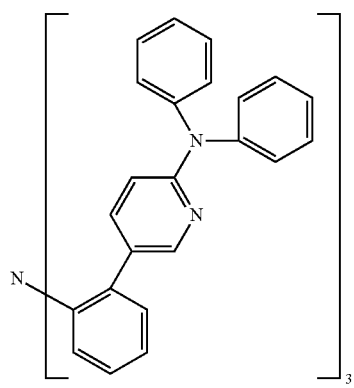
(28)
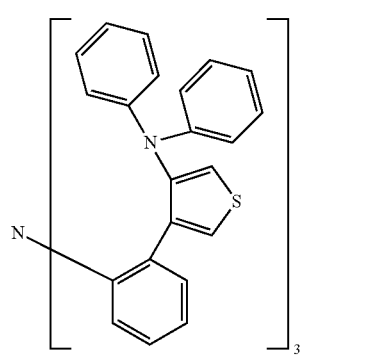
(29)
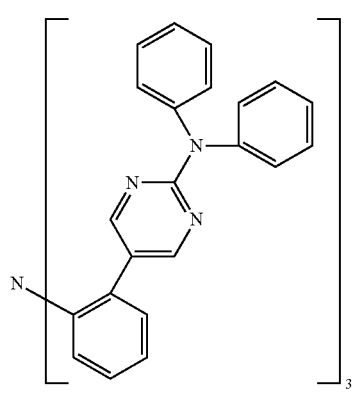
(30)

-continued
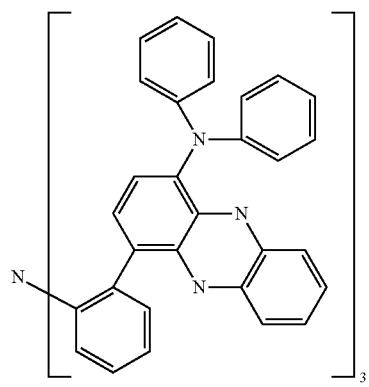
(31)
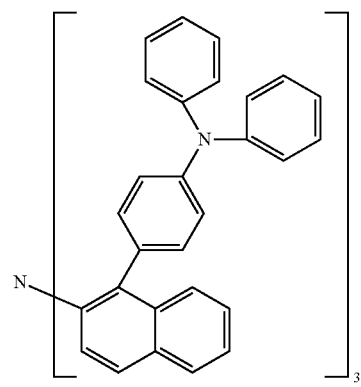
(32)
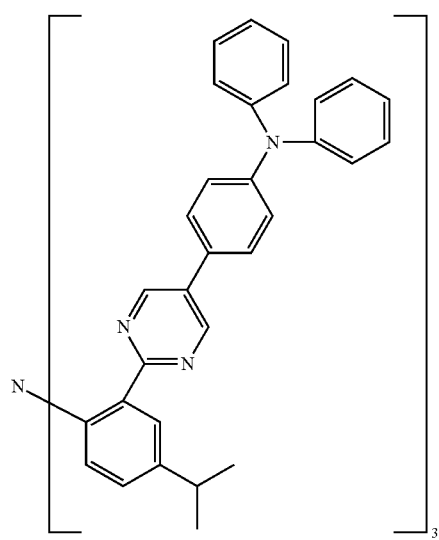
(33)
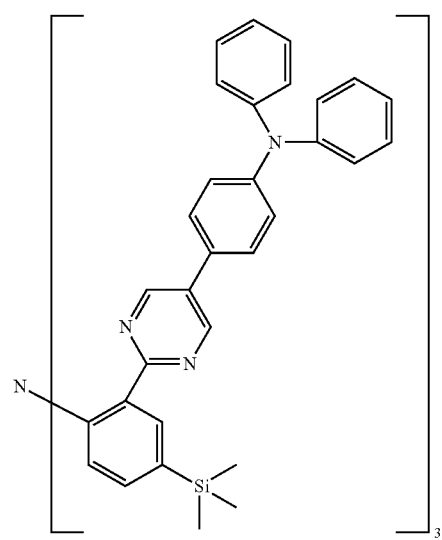
(34)
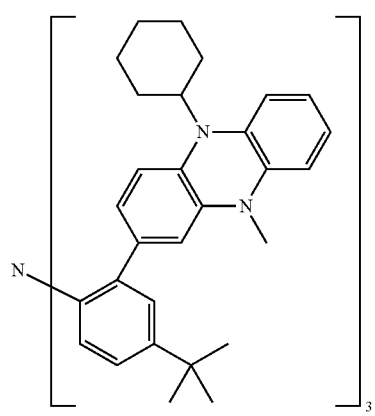
(35)
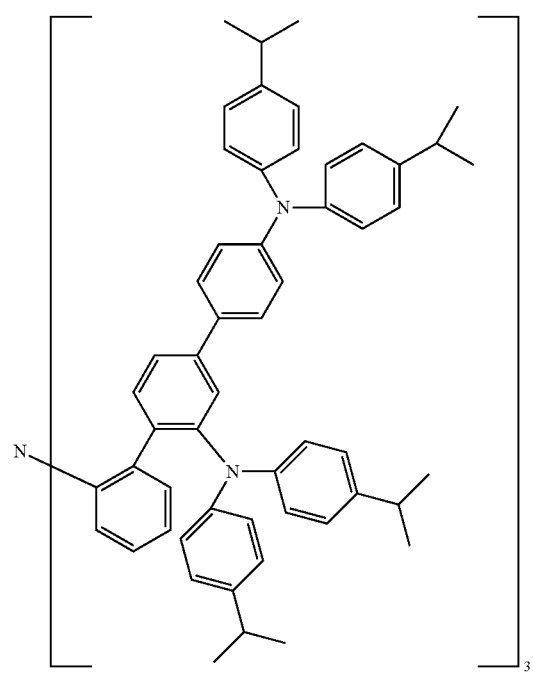
(36)

-continued
(37)
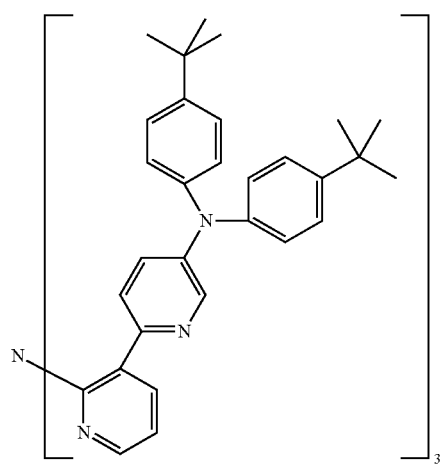
(38)
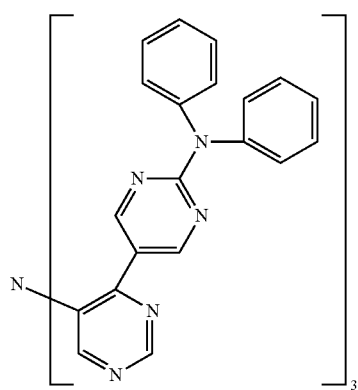
(39)
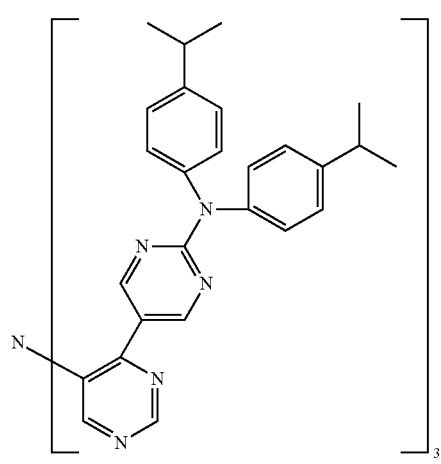
(40)
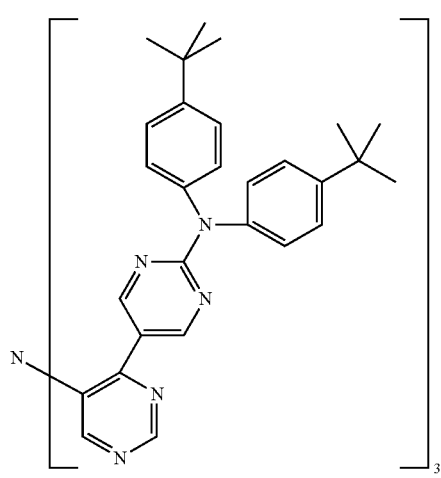
(41)
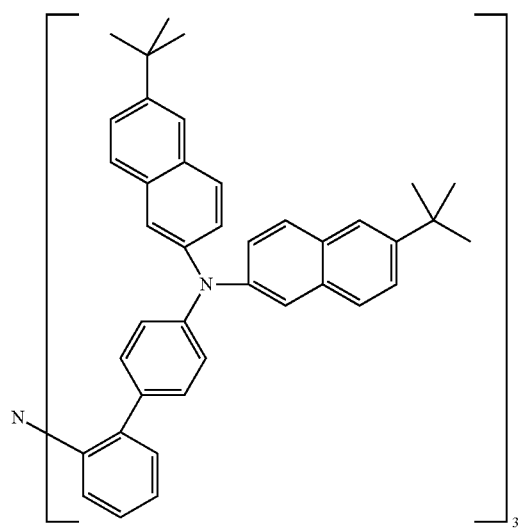
(42)
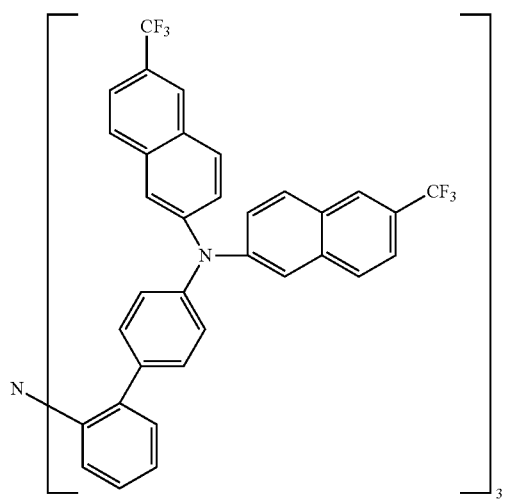

-continued
(43)
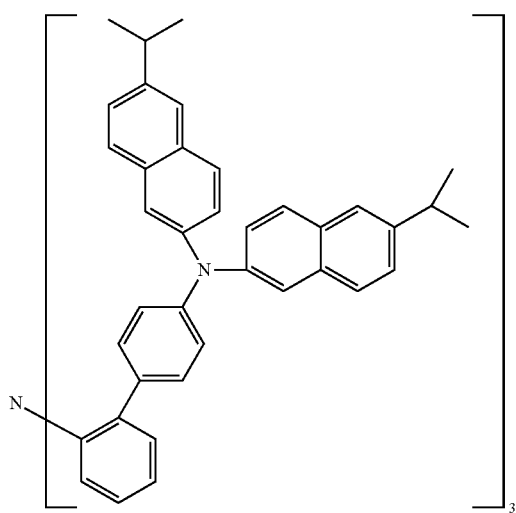
(44)
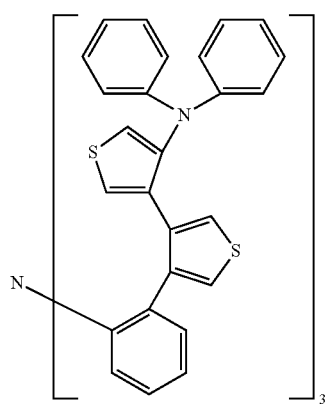
(45)
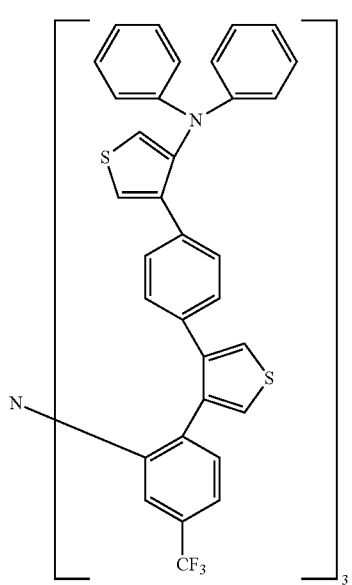
(46)
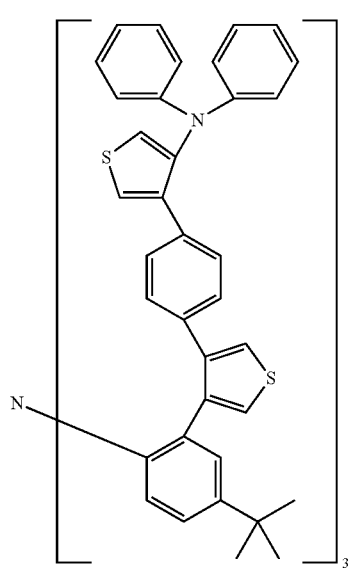

-continued
(47) 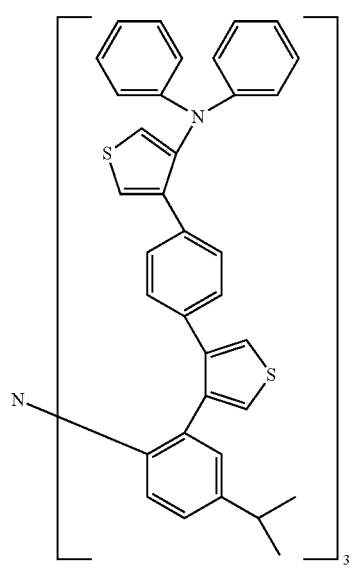
(48) 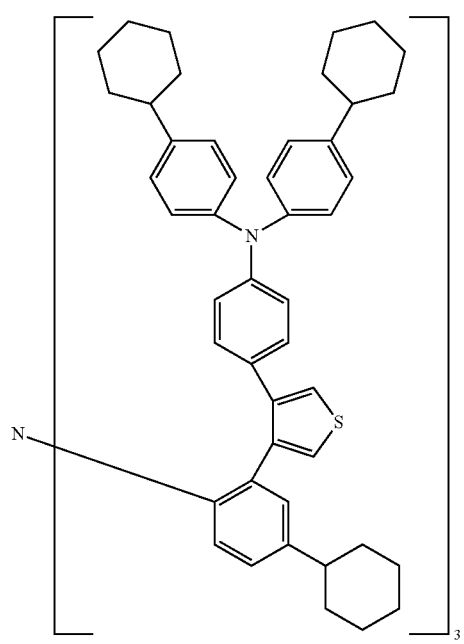
(49) 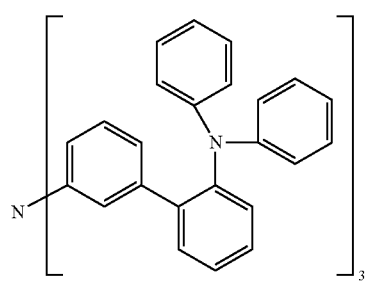
(50) 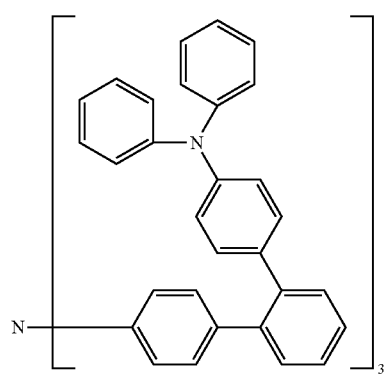
(51) 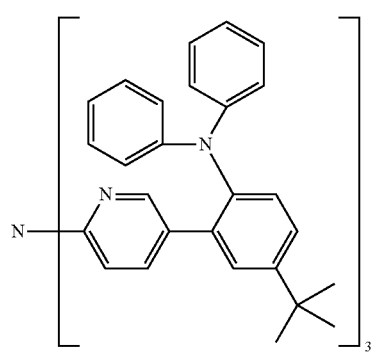
(52) 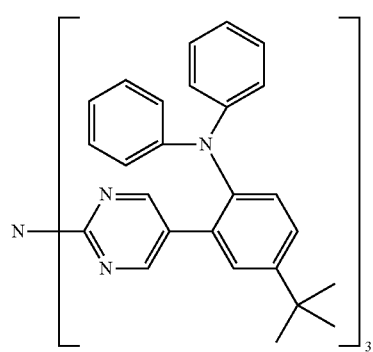

-continued
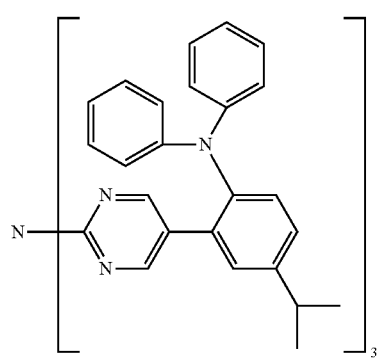
(53)
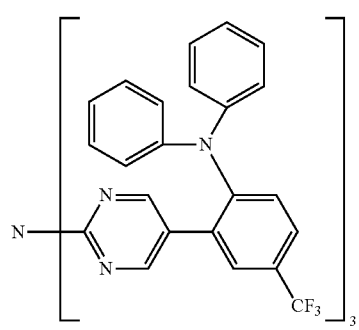
(54)
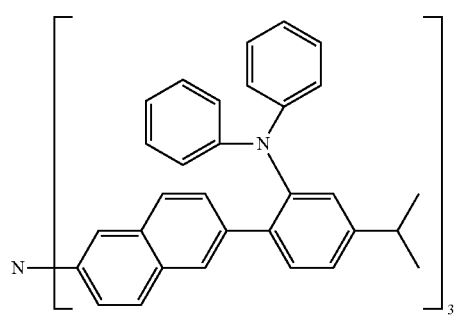
(55)
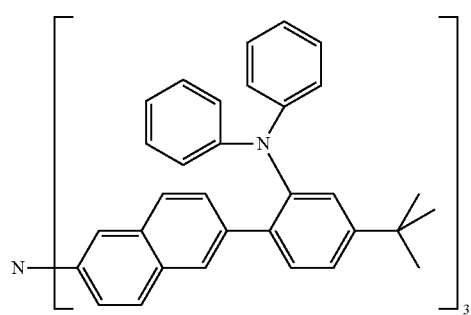
(56)
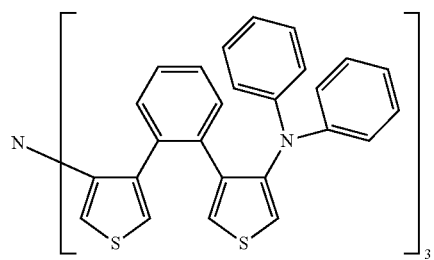
(57)
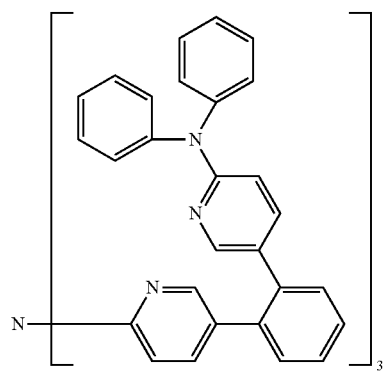
(58)
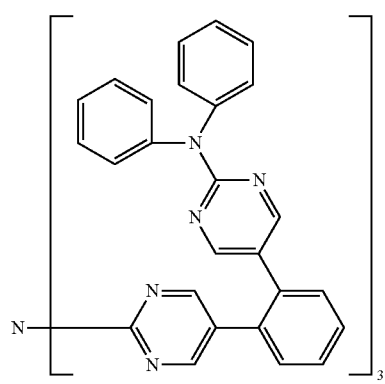
(59)
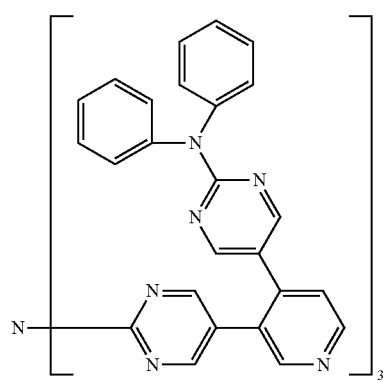
(60)

-continued
(61)
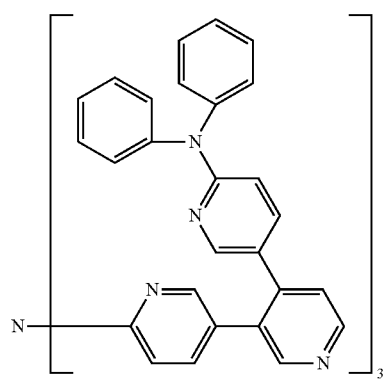
(62)
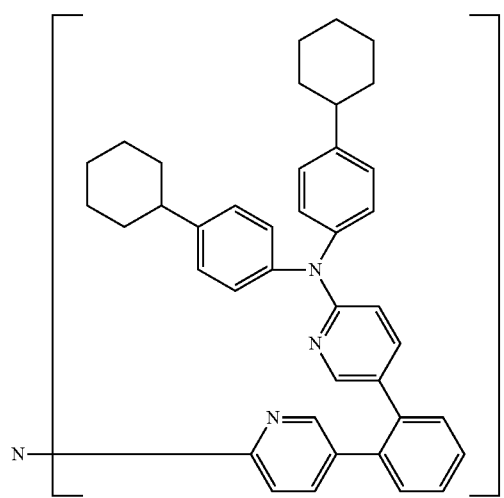
(63)
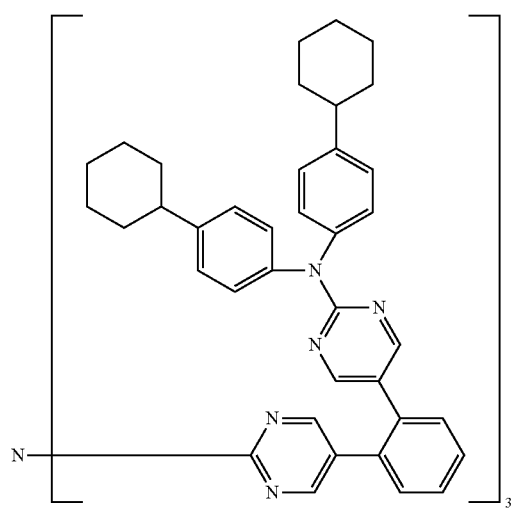
(64)
(65)
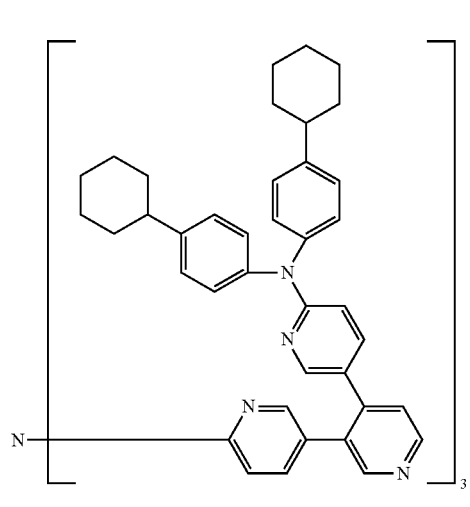
(66)
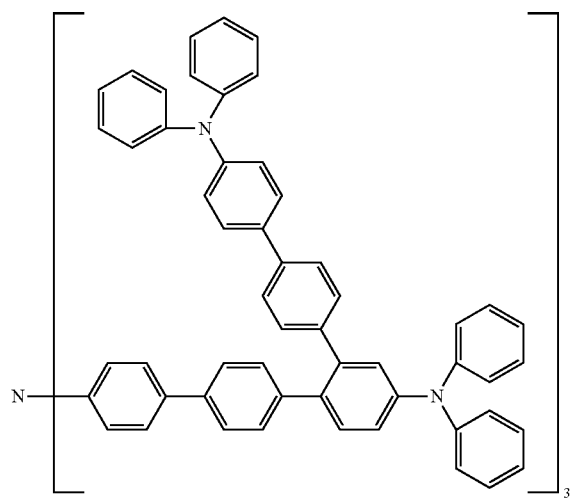

-continued
(67)
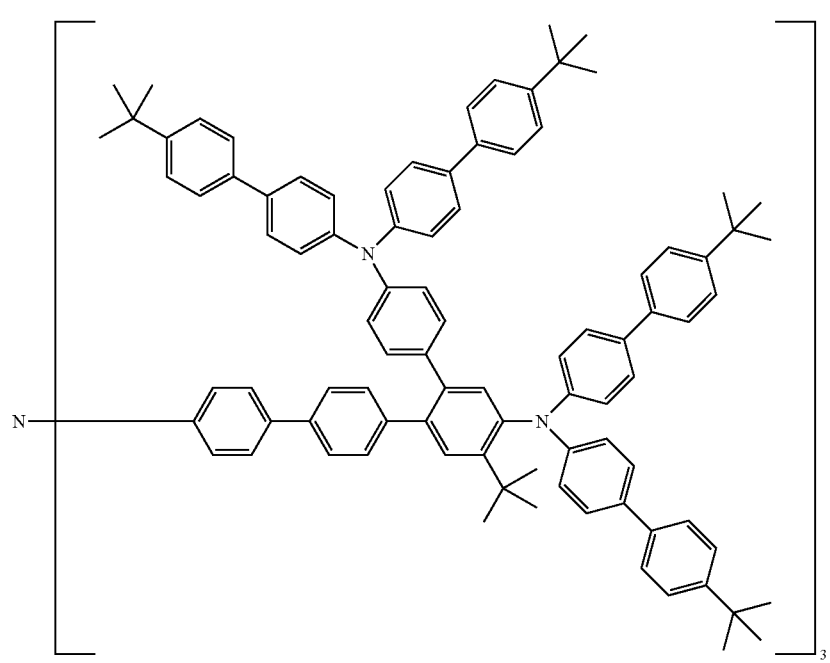
(68)

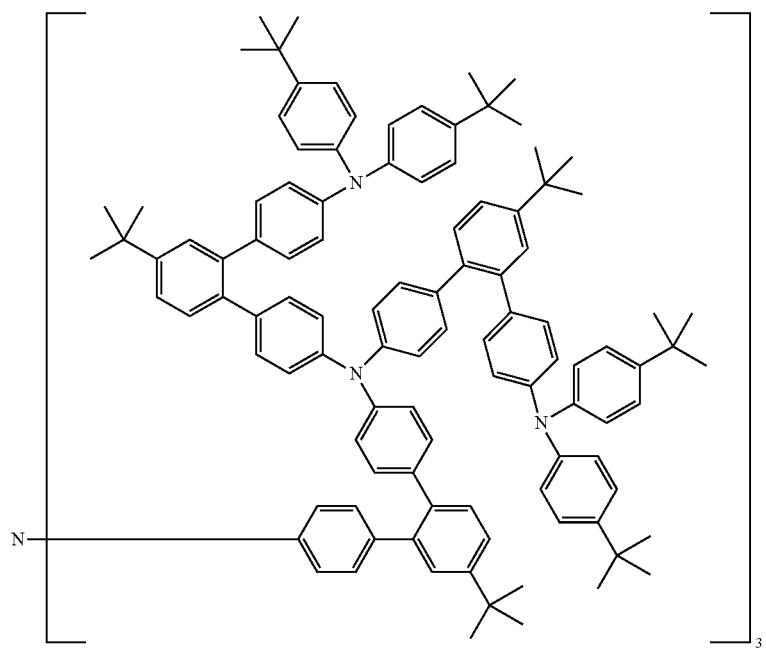
(69)
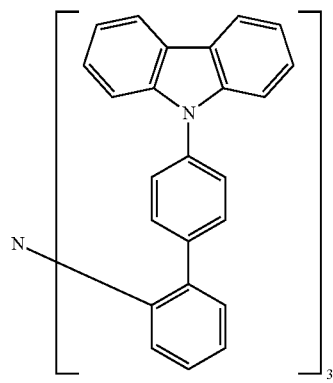
(70)
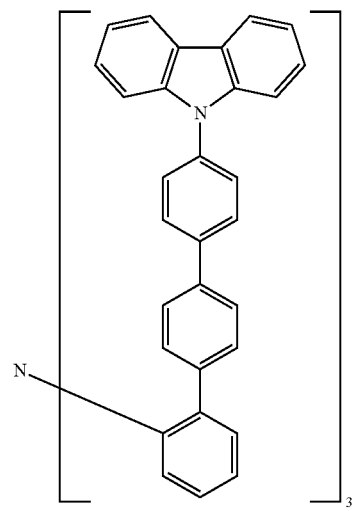
(71)

-continued
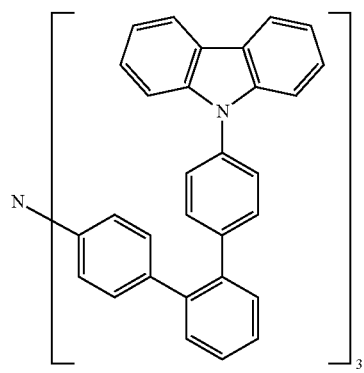 (72)
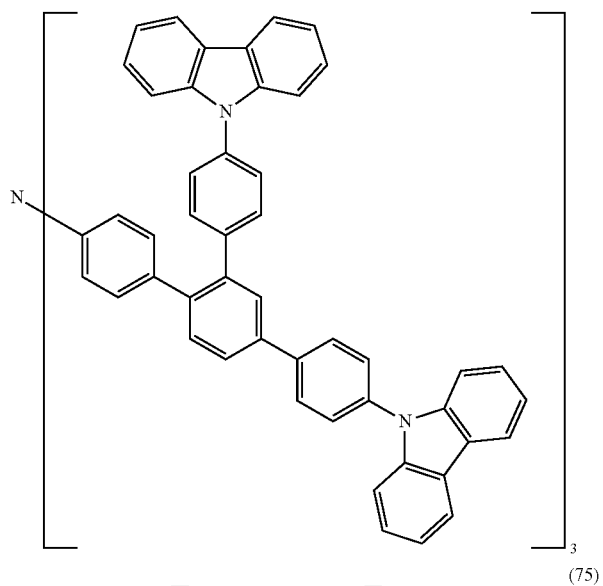 (73)
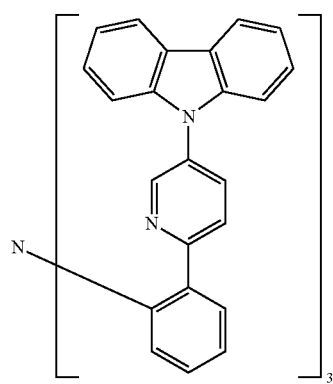 (74)
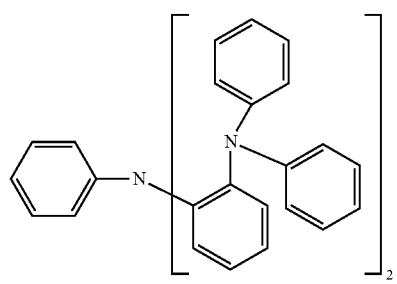 (75)
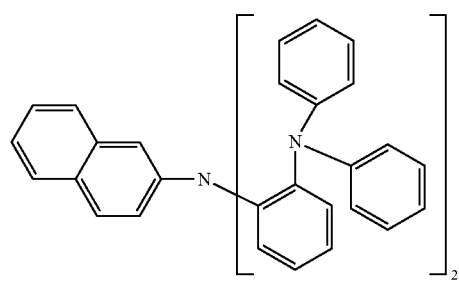 (76)
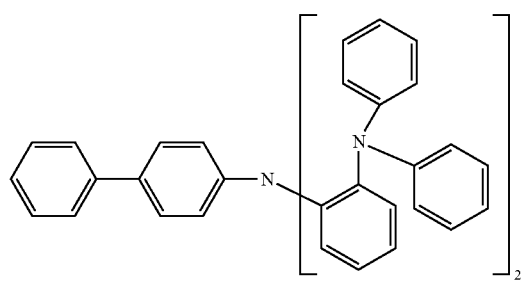 (77)
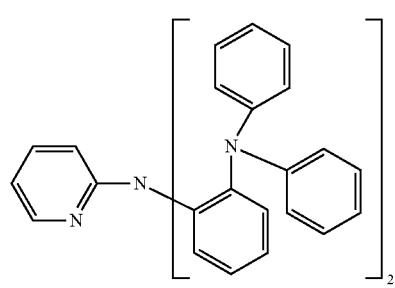 (78)
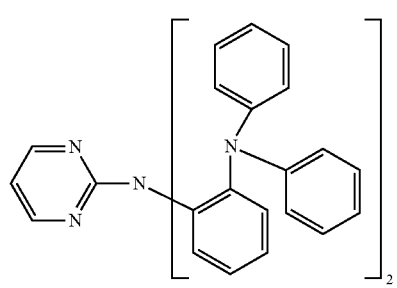 (79)

-continued
(80)
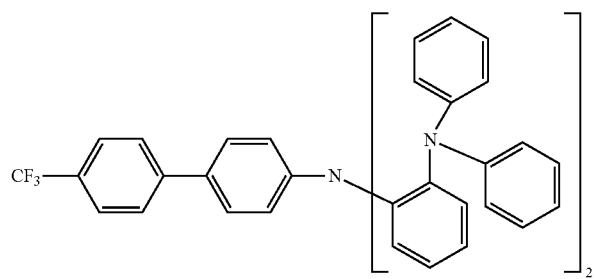
(81)
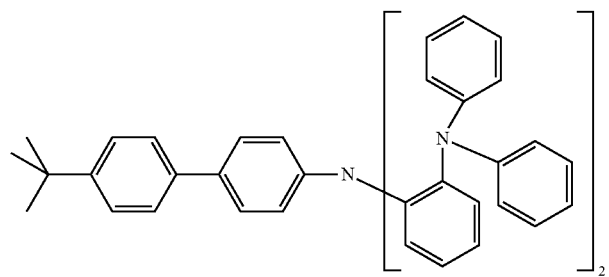
(82)
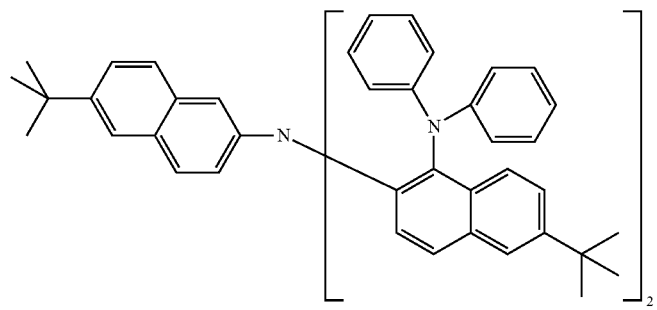
(83)
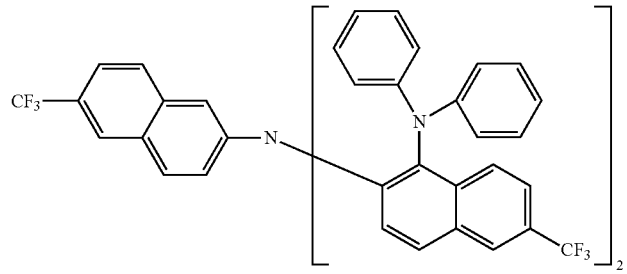
(84)
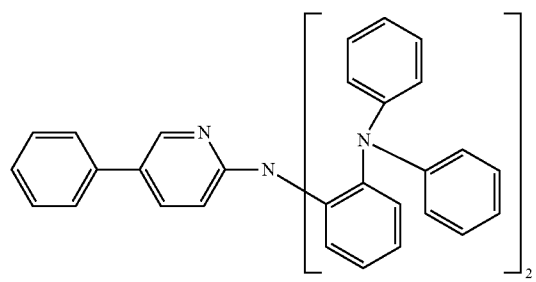
(85)
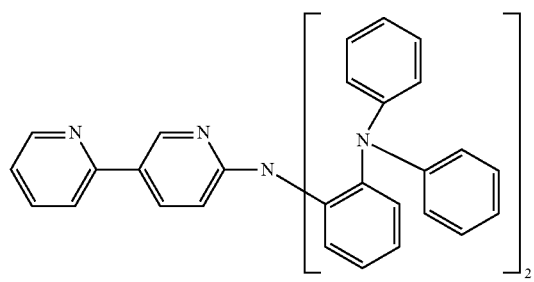

-continued
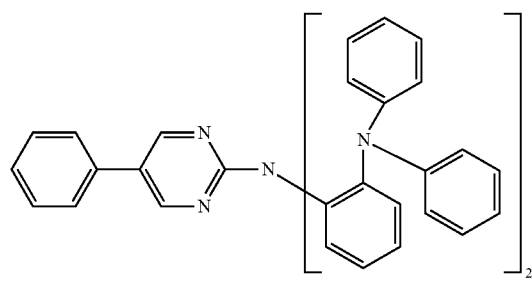
(86)
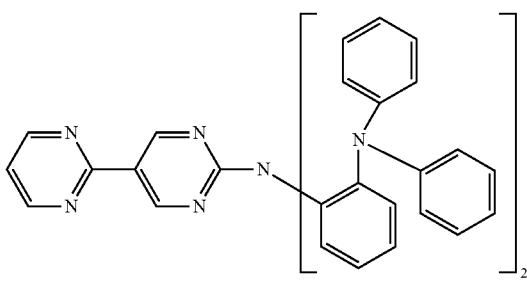
(87)
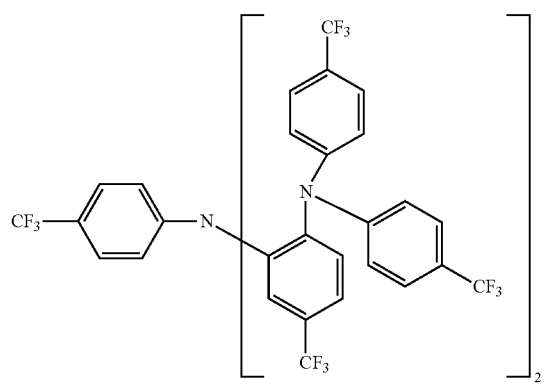
(88)
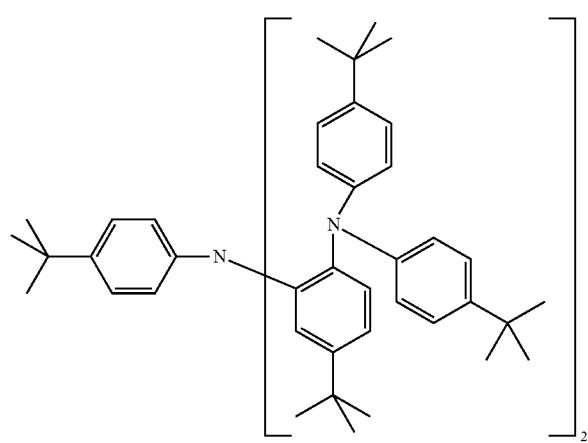
(89)

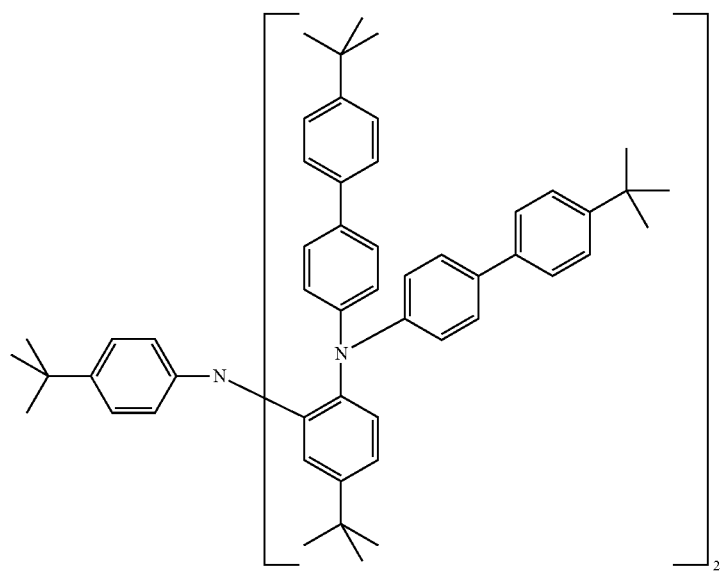
(90)
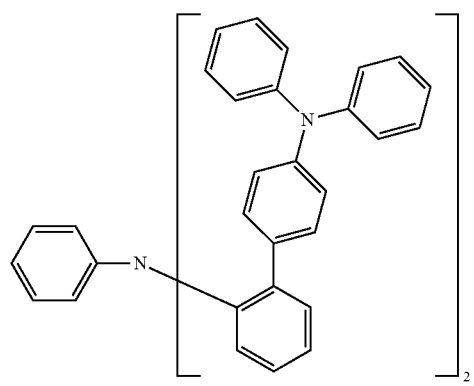
(91)
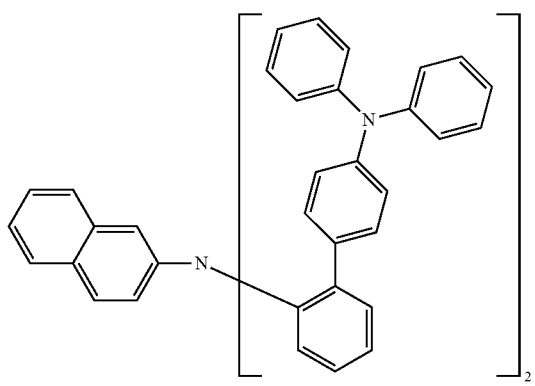
(92)
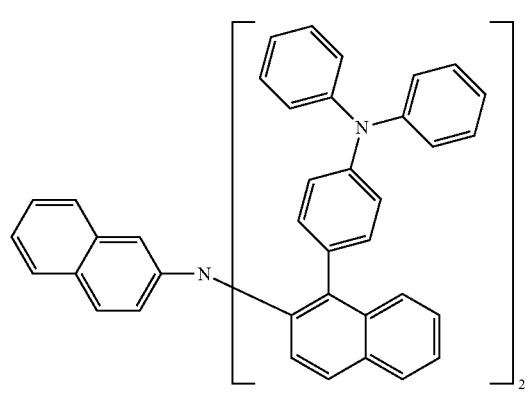
(93)
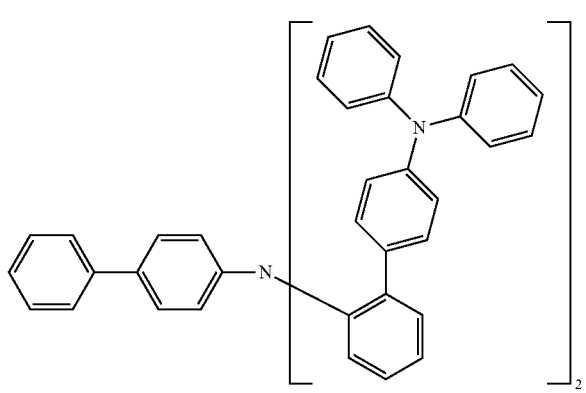
(94)

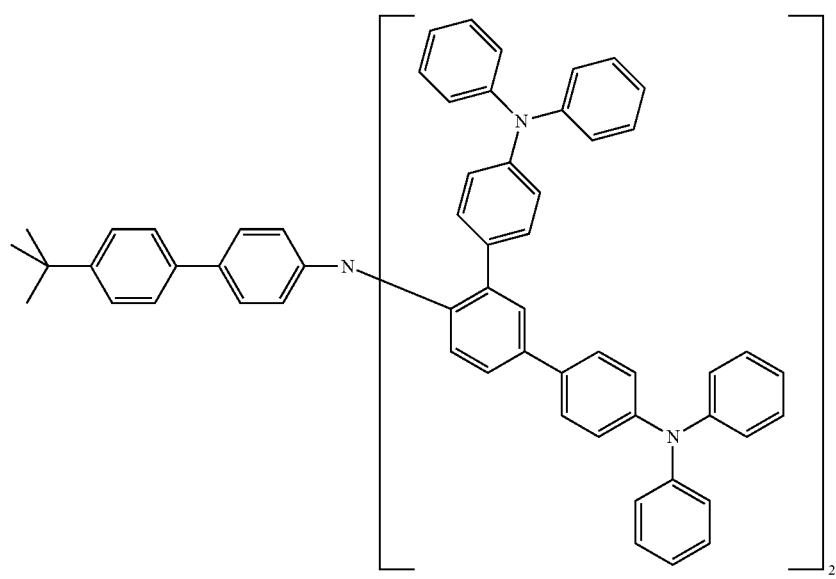
(95)
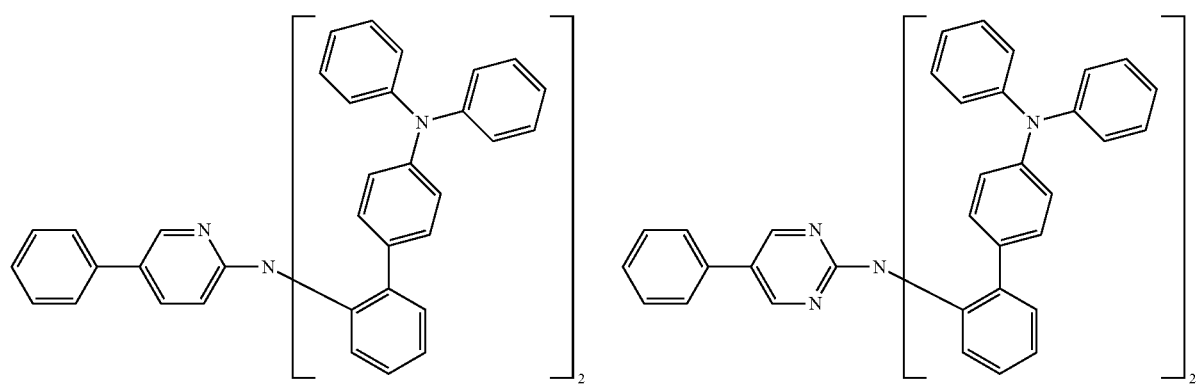
(96) (97)
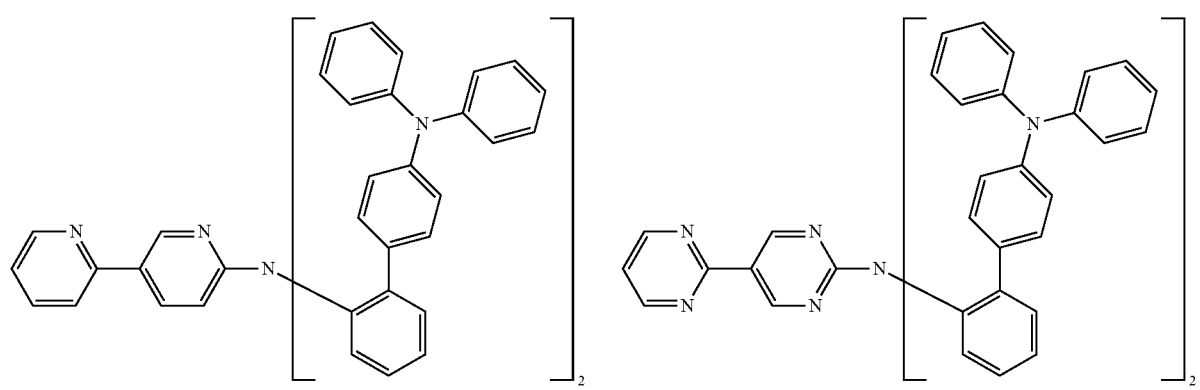
(98) (99)

-continued
(100)
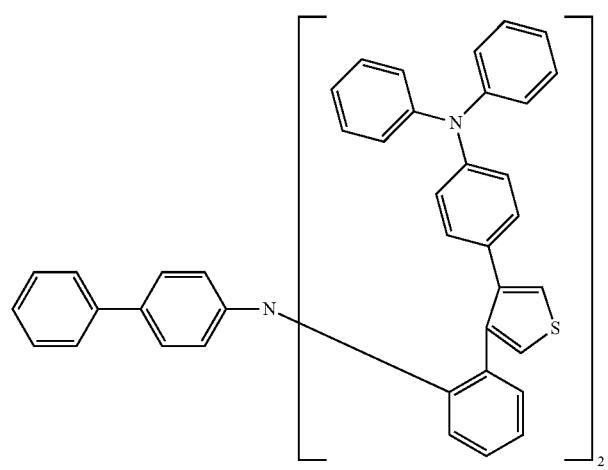
(101)
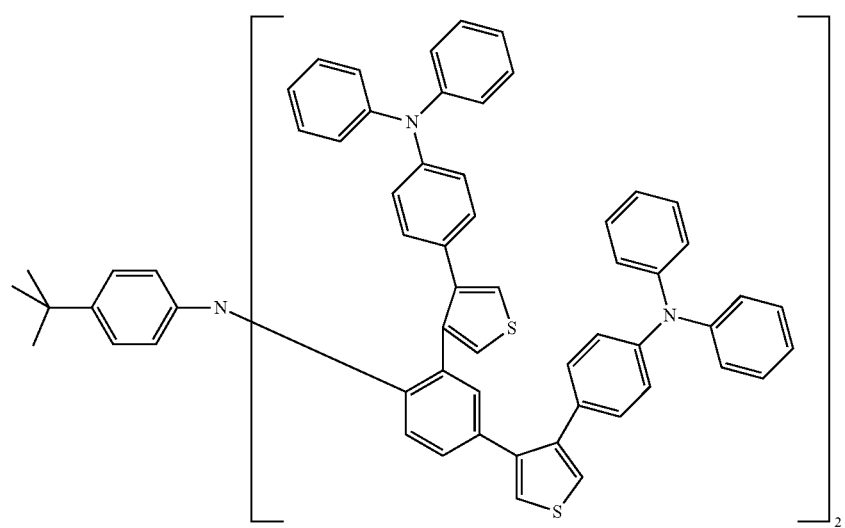
(102)
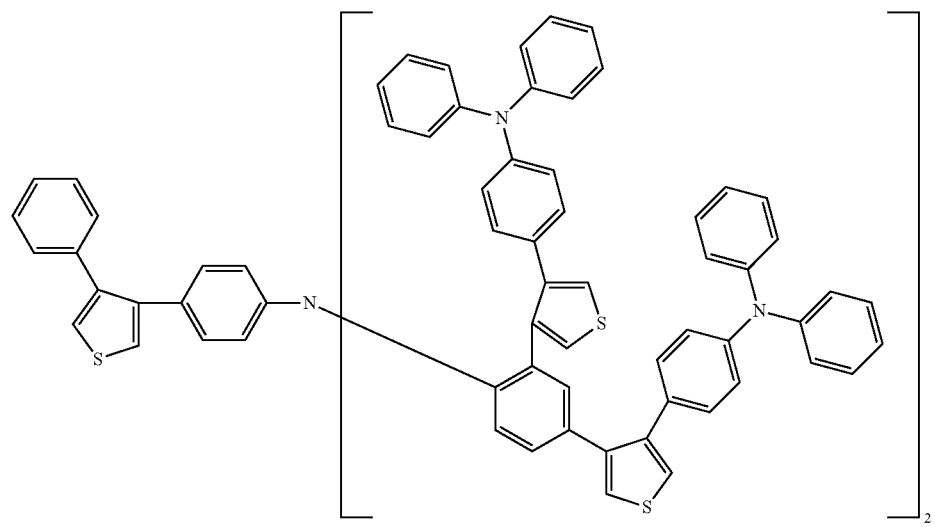

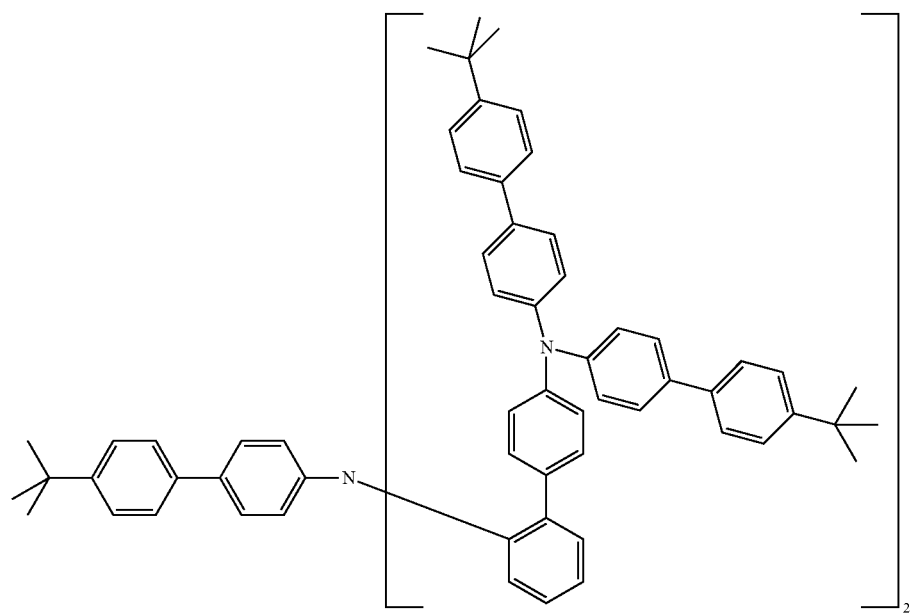
(103)
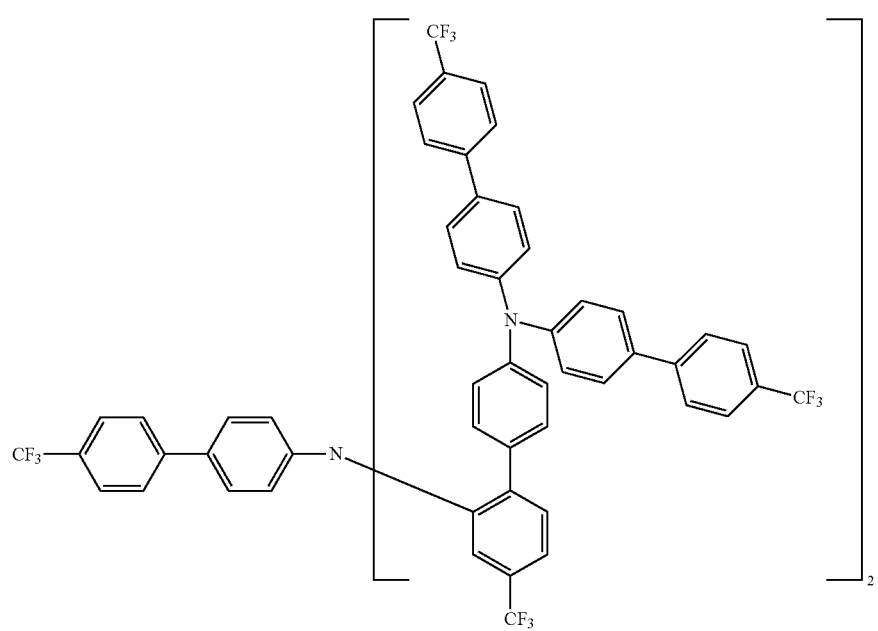
(104)

-continued
(105)
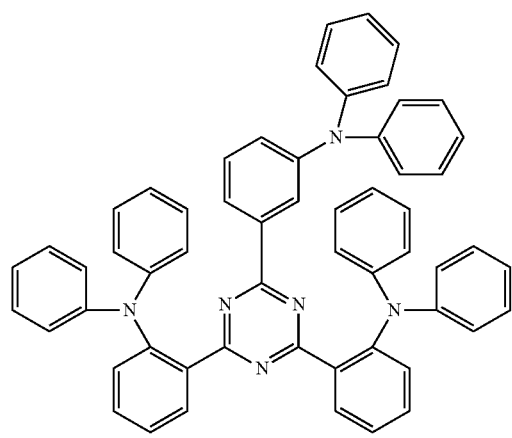
(106)
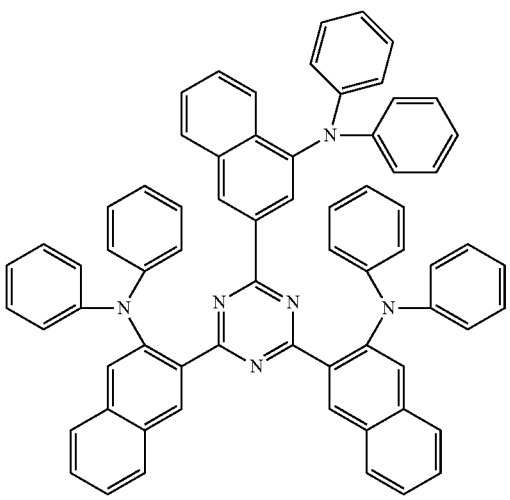
(107)
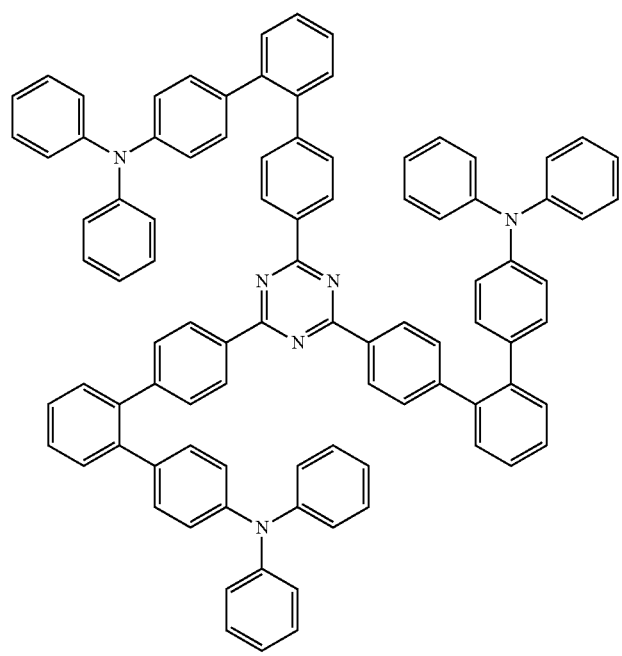

(108)
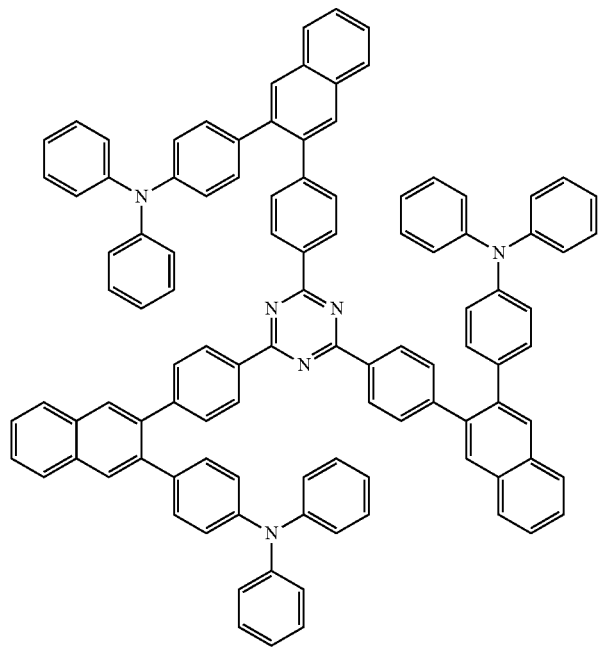
(109)
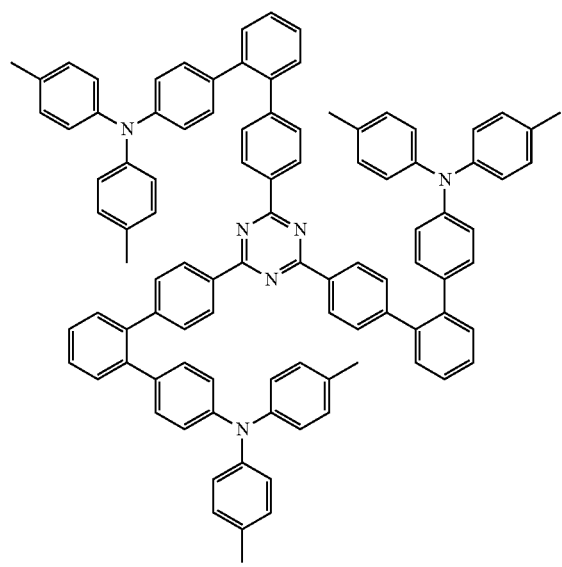
(110)
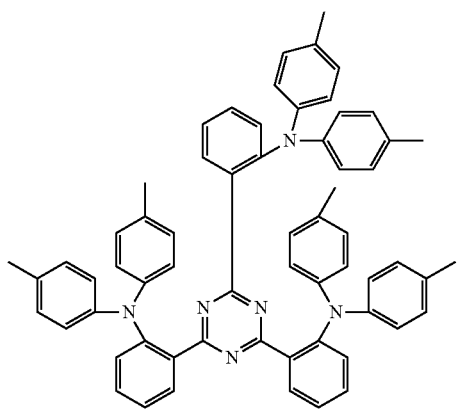
(111)
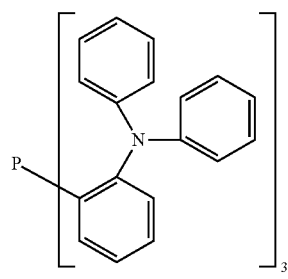
(112)
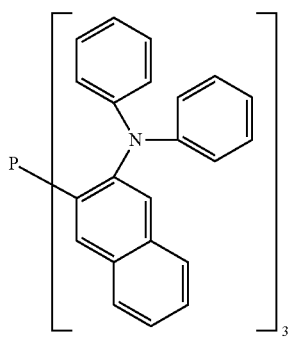

-continued
(113) 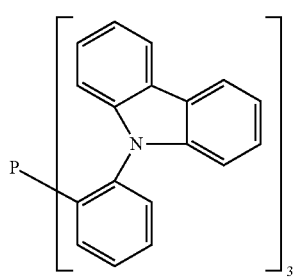
(114) 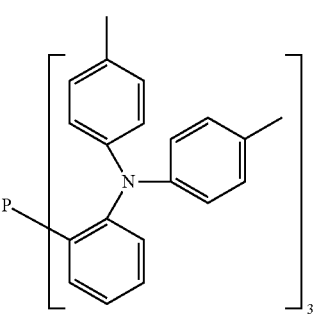
(115) 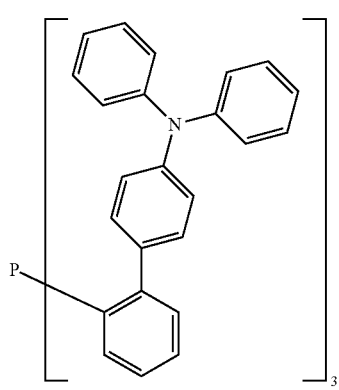
(116) 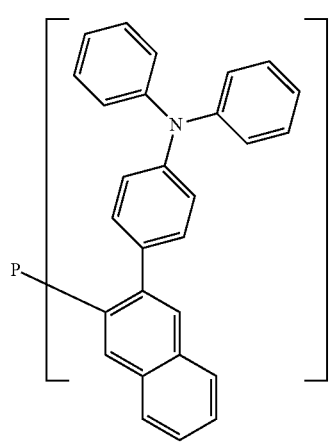
(117) 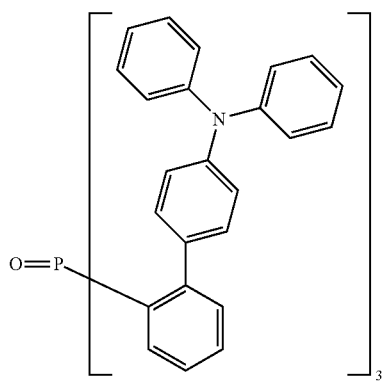
(118) 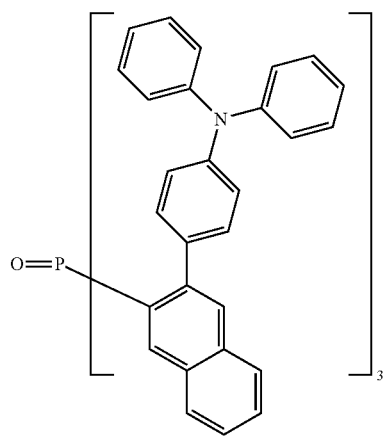
(119) 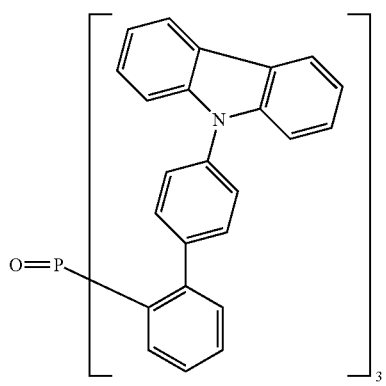
(120) 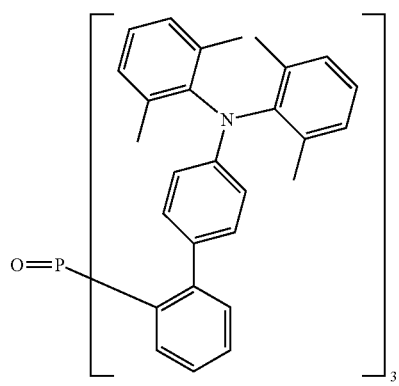

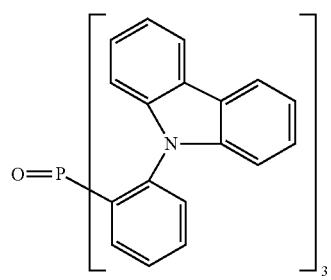

(121)

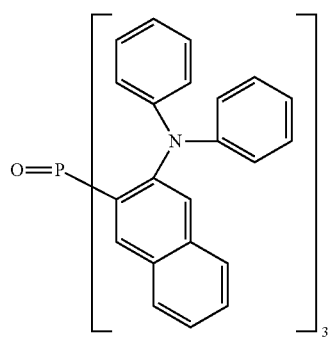

(122)

The compounds according to the invention can be synthesised using synthetic steps known to the person skilled in the art. It has proven particularly suitable here to start from the central triarylamine or a corresponding derivative containing other groups X which is substituted by a reactive leaving group, in particular chlorine, bromine, iodine, tosylate or triflate, in the ortho-position to the aryl groups. A boronic acid derivative of the group $(Ar^3)_2N$—$Ar^2$ can then be coupled to this group in a Suzuki coupling with palladium catalysis. The group $(Ar^3)_2$—NH can likewise be coupled to this group in a Hartwig-Buchwald coupling. These types of reaction are adequately known to the person skilled in the art of organic synthesis, and he will be able to use them for the synthesis of the compounds according to the invention without an inventive step.

The invention therefore furthermore relates to a process for the preparation of the compounds according to the invention, comprising either the introduction of the group $(Ar^3)_2N$—$Ar^2$ as boronic acid derivative in a Suzuki coupling or the introduction of the group $(Ar^3)_2N$ as $(Ar^3)_2NH$ in a Hartwig-Buchwald coupling.

The compounds according to the invention described above, in particular compounds which are substituted by reactive leaving groups, such as bromine, iodine, triflate, tosylate, boronic acid or boronic acid ester, can be used as monomers for the production of corresponding dimers, trimers, tetramers, pentamers, oligomers, polymers or as the core of dendrimers. The oligomerisation or polymerisation here preferably takes place via the halogen functionality or the boronic acid functionality. This applies, in particular, to compounds in which the radicals $R^1$ each stand for a reactive leaving group.

The invention therefore furthermore relates to dimers, trimers, tetramers, pentamers, oligomers, polymers or dendrimers comprising one or more compounds of the formula (1), where one or more radicals $R^1$ or $R^2$ represent bonds between the compounds of the formula (1) in the dimer, trimer, tetramer or pentamer or bonds from the compound of the formula (1) to the polymer, oligomer or dendrimer. An oligomer in the sense of this invention is taken to mean a compound which has at least six units of the formula (1). The polymers, oligomers or dendrimers may be conjugated, partially conjugated or non-conjugated. The trimers, tetramers, pentamers, oligomers or polymers may be linear or branched. In the linearly linked structures, the units of the formula (1) can be linked directly to one another or linked to one another via a divalent group, for example via a substituted or unsubstituted alkylene group, via a heteroatom or via a divalent aromatic or heteroaromatic group. In branched structures, for example, three or more units of the formula (1) may be linked via a trivalent or polyvalent group, for example via a trivalent or polyvalent aromatic or heteroaromatic group, to give a branched trimer, tetramer, pentamer, oligomer or polymer.

For the recurring units of the formula (1) in dimers, trimers, tetramers, pentamers, oligomers, polymers and dendrimers, the same preferences apply as described above. Preferred recurring units are therefore again the units of the formulae (2), (3), (4) and (5).

For the preparation of the oligomers, polymers or dendrimers, the monomers according to the invention are homopolymerised or copolymerised with further monomers. Suitable and preferred comonomers are selected from fluorenes (for example in accordance with EP 842208 or WO 00/22026), spirobifluorenes (for example in accordance with EP 707020, EP 894107 or WO 06/061181), para-phenylenes (for example in accordance with WO 92/18552), carbazoles (for example in accordance with WO 04/070772 or WO 04/113468), thiophenes (for example in accordance with EP 1028136), dihydrophenanthrenes (for example in accordance with WO 05/014689), cis- and trans-indenofluorenes (for example in accordance with WO 04/041901 or WO 04/113412), ketones (for example in accordance with WO 05/040302), phenanthrenes (for example in accordance with WO 05/104264 or WO 07/017,066) or also a plurality of these units. The polymers, oligomers and dendrimers usually also contain further units, for example emitting (fluorescent or phosphorescent) units, such as, for example, vinyltriarylamines (for example in accordance with WO 07/068,325) or phosphorescent metal complexes (for example in accordance with WO 06/003000), and/or charge-transport units. The recurring units according to the invention are particularly suitable as charge-transport units for holes.

The present invention furthermore relates to mixtures comprising at least one compound of the formula (1) or a corresponding dimer, trimer, tetramer, pentamer, oligomer or polymer and at least one further compound. The further compound can be, for example, a fluorescent or phosphorescent dopant if the compound of the formula (1) is used as matrix material. Suitable fluorescent and phosphorescent dopants are mentioned below in connection with the organic electroluminescent devices and are also preferred for the mixtures according to the invention. The further compound can also be a dopant if the compound of the formula (1) is a hole-transport or electron-transport compound. Suitable dopants are mentioned below in connection with the organic electroluminescent devices.

The present invention still furthermore relates to formulations and solutions comprising at least one compound of the formula (1) or a corresponding dimer, trimer, tetramer, pentamer, oligomer or polymer and at least one solvent, where the solvent is usually an organic solvent. Solutions of this type are necessary for the production of the electronic device from solution, for example by spin coating or by printing processes. These solutions may also comprise mixtures of compounds of the present invention.

The compounds of the formula (1) according to the invention and corresponding dimers, trimers, tetramers, pentamers, oligomers, polymers or dendrimers are suitable for use in electronic devices, in particular in organic electroluminescent devices (OLEDs, PLEDs). Depending on the substitution, the compounds are employed in different functions and layers.

An electronic device in the sense of this invention comprises at least one anode, at least one cathode and at least one layer comprising at least one organic compound between the anode and the cathode.

The invention therefore furthermore relates to the use of compounds of the formula (1) or corresponding dimers, trimers, tetramers, pentamers, oligomers, polymers or dendrimers in electronic devices, in particular in organic electroluminescent devices.

The invention still furthermore relates to electronic devices comprising at least one compound of the formula (1) or a corresponding dimer, trimer, tetramer, pentamer, oligomer, polymer or dendrimer, in particular organic electroluminescent devices, comprising an anode, a cathode and at least one emitting layer, characterised in that at least one organic layer, which may be an emitting layer or another layer, comprises at least one compound of the formula (1) or a corresponding dimer, trimer, tetramer, pentamer, oligomer, polymer or dendrimer.

The present application text is predominantly directed to the use of the compounds according to the invention with respect to OLEDs and PLEDs and the corresponding displays. In spite of this restriction of the description, it is possible for the person skilled in the art, without further inventive step, also to employ the compounds according to the invention in other electronic devices, for example in organic field-effect transistors (O-FETs), organic thin-film transistors (O-TFTs), organic light-emitting transistors (O-LETs), organic integrated circuits (O-ICs), organic solar cells (O-SCs), organic field-quench devices (O-FQDs), light-emitting electrochemical cells (LECs), organic laser diodes (O-lasers) or organic photoreceptors.

The present invention likewise relates to the use of the compounds according to the invention in the corresponding devices and to these devices themselves.

Apart from the cathode, anode and emitting layer(s), the organic electroluminescent device may also comprise further layers. These are selected, for example, from in each case one or more hole-injection layers, hole-transport layers, hole-blocking layers, electron-transport layers, electron-injection layers, electron-blocking layers, exciton-blocking layers, charge-generation layers (IDMC 2003, Taiwan; Session 21 OLED (5), T. Matsumoto, T. Nakada, J. Endo, K. Mori, N. Kawamura, A. Yokoi, J. Kido, Multi-photon Organic EL Device Having Charge Generation Layer) and/or organic or inorganic p/n junctions. Furthermore, the layers, in particular the charge-transport layers, may also be doped. The doping of the layers may be advantageous for improved charge transport. However, it should be pointed out that each of these layers does not necessarily have to be present, and the choice of layers is always dependent on the compounds used and in particular also on whether the electroluminescent device is fluorescent or phosphorescent.

In an embodiment of the invention, the organic electroluminescent device comprises a plurality of emitting layers, where at least one organic layer comprises at least one compound of the formula (1). These emission layers particularly preferably have in total a plurality of emission maxima between 380 nm and 750 nm, resulting overall in white emission, i.e. various emitting compounds which are able to fluoresce or phosphoresce and which emit blue, green, yellow, orange or red light are used in the emitting layers. Particular preference is given to three-layer systems, i.e. systems having three emitting layers, where at least one of these layers comprises at least one compound of the formula (1) and where the three layers exhibit blue, green and orange or red emission (for the basic structure, see, for example, WO 05/011013). Preference is furthermore given to the use of more than three emitting layers. Emitters which have broad-band emission bands and thus exhibit white emission are likewise suitable for white emission.

In a preferred embodiment of the invention, the compounds of the formula (1) are employed as matrix material for fluorescent or phosphorescent compounds in an emitting layer. In the case of a matrix material for fluorescent compounds, one or more groups $R^1$ preferably stand for an aromatic or heteroaromatic ring system, in particular for an aromatic ring system containing anthracene.

A matrix material in a system comprising matrix and dopant is taken to mean the component which is present in the higher proportion in the system. In a system comprising a matrix and a plurality of dopants, the matrix is taken to mean the component whose proportion in the mixture is the highest.

The compound of the formula (1) can also be employed as a component in a mixture of a plurality of matrix materials ("mixed host"), where the emitter here can also be a fluorescent or phosphorescent emitter. If the compound of the formula (1) is employed in a mixture of a plurality of matrix materials, this compound is usually the hole-conducting component. Matrix materials for phosphorescent emitters with which the compound of the formula (1) can be combined are preferably selected from the group consisting of CBP (N,N-biscarbazolylbiphenyl), carbazole derivatives (for example in accordance with WO 05/039246, US 2005/0069729, JP 2004/288381, EP 1205527 or WO 08/086,851), azacarbazoles (for example in accordance with EP 1617710, EP 1617711, EP 1731584, JP 2005/347160), ketones (for example in accordance with WO 04/093207 or the unpublished application DE 102008033943.1), phosphine oxides, sulfoxides and sulfones (for example in accordance with WO 05/003253), oligophenylenes, aromatic amines (for example in accordance with US 2005/0069729), bipolar matrix materials (for example in accordance with WO 07/137,725), silanes (for example in accordance with WO 05/111172), 9,9-diarylfluorene derivatives (for example in accordance with the unpublished application DE 102008017591.9), azaboroles, boronic esters (for example in accordance with WO 06/117052), indolocarbazoles (WO 07/063,754, WO 08/056,746), triazine derivatives (WO 07/063,754 or the unpublished application DE 102008036982.9) or zinc complexes (EP 652273 or the unpublished application DE 102007053771.0).

If the compound of the formula (1) is employed as matrix material for an emitting compound in an emitting layer, it can be employed in combination with one or more fluorescent materials or phosphorescent materials (triplet emitters). Phosphorescence in the sense of this invention is taken to mean the luminescence from an excited state of relatively high spin multiplicity, i.e. a spin state >1, in particular from an excited triplet state. For the purposes of this invention, all luminescent Ir and Pt compounds are regarded as phosphorescent compounds. If the compound of the formula (1) is employed as matrix for a phosphorescent emitter, X preferably stands for N, P=O or triazine. The mixture of the compound of the formula (1) and the phosphorescent compound then comprises between 99 and 1% by vol., preferably between 98 and 10% by vol., particularly preferably between 97 and 60% by vol., in particular between 95 and 85% by vol., of the compound of the formula (1), based on the entire mixture of emitter and matrix material. Correspondingly, the mixture comprises between 1 and 99% by vol., preferably between 2 and 90% by vol., particularly preferably between 3 and 40% by vol., in particular between 5 and 15% by vol., of the emitter, based on the entire mixture of emitter and matrix material.

Suitable phosphorescent compounds (=triplet emitters) are, in particular, compounds which emit light, preferably in the visible region, on suitable excitation and in addition contain at least one atom having an atomic number of greater than 20, preferably greater than 38 and less than 84, particularly preferably greater than 56 and less than 80. The phosphorescence emitters used are preferably compounds which contain copper, molybdenum, tungsten, rhenium, ruthenium, osmium, rhodium, iridium, palladium, platinum, silver, gold or europium, in particular compounds which contain iridium or platinum.

Examples of the emitters described above are revealed by the applications WO 00/70655, WO 01/41512, WO 02/02714, WO 02/15645, EP 1191613, EP 1191612, EP 1191614 and WO 05/033244. In general, all phosphorescent complexes as used in accordance with the prior art for phosphorescent OLEDs and as are known to the person skilled in the art in the area of organic electroluminescence are suitable, and the person skilled in the art will be able to use further phosphorescent complexes without an inventive step.

If the compound of the formula (1) is employed as matrix material for fluorescent compounds, the proportion of the matrix material in the emitting layer is between 50.0 and 99.9% by vol., preferably between 80.0 and 99.5% by vol., particularly preferably between 90.0 and 99.0% by vol. Correspondingly, the proportion of the dopant is between 0.1 and 50.0% by vol., preferably between 0.5 and 20.0% by vol., particularly preferably between 1.0 and 10.0% by vol.

Preferred dopants are selected from the class of the monostyrylamines, the distyrylamines, the tristyrylamines, the tetrastyrylamines, the styryl-phosphines, the styryl ethers and the arylamines. A monostyrylamine is taken to mean a compound which contains one substituted or unsubstituted styryl group and at least one, preferably aromatic, amine. A distyrylamine is taken to mean a compound which contains two substituted or unsubstituted styryl groups and at least one, preferably aromatic, amine. A tristyrylamine is taken to mean a compound which contains three substituted or unsubstituted styryl groups and at least one, preferably aromatic, amine. A tetrastyrylamine is taken to mean a compound which contains four substituted or unsubstituted styryl groups and at least one, preferably aromatic, amine. The styryl groups are particularly preferably stilbenes, which may also be further substituted. Corresponding phosphines and ethers are defined analogously to the amines. An arylamine or aromatic amine in the sense of this invention is taken to mean a compound which contains three substituted or unsubstituted aromatic or heteroaromatic ring systems bonded directly to the nitrogen. At least one of these aromatic or heteroaromatic ring systems is preferably a condensed ring system, preferably having at least 14 aromatic ring atoms. Preferred examples thereof are aromatic anthracenamines, aromatic anthracenediamines, aromatic pyrenamines, aromatic pyrenediamines, aromatic chrysenamines or aromatic chrysenediamines. An aromatic anthracenamine is taken to mean a compound in which one diarylamino group is bonded directly to an anthracene group, preferably in the 9-position. An aromatic anthracenediamine is taken to mean a compound in which two diarylamino groups are bonded directly to an anthracene group, preferably in the 2,6- or 9,10-position. Aromatic pyrenamines, pyrenediamines, chrysenamines and chrysenediamines are defined analogously thereto, where the diarylamino groups on the pyrene are preferably bonded in the 1-position or in the 1,6-position. Further preferred dopants are selected from indenofluorenamines or indenofluorenediamines, for example in accordance with WO 06/122630, benzoindenofluorenamines or benzoindenofluorenediamines, for example in accordance with WO 08/006, 449, and dibenzoindenofluorenamines or dibenzoindenofluorenediamines, for example in accordance with WO 07/140,847. Examples of dopants from the class of the styrylamines are substituted or unsubstituted tristilbenamines or the dopants described in WO 06/000388, WO 06/058737, WO 06/000389, WO 07/065,549 and WO 07/115,610. Further preferred dopants are aromatic hydrocarbons, such as, for example, the compounds disclosed in the unpublished application DE 102008035413.9.

In a further embodiment of the invention, the compounds of the formula (1) are employed as hole-transport material or as hole-injection material or as electron-blocking material or as exciton-blocking material. In such compounds, X preferably stands for N or $N(Ar^2)_3$. The compound is then preferably employed in a hole-transport or hole-injection or electron-blocking or exciton-blocking layer. A hole-injection layer in the sense of this invention is a layer which is directly adjacent to the anode. A hole-transport layer in the sense of this invention is a layer which is located between a hole-injection layer and an emission layer. An electron-blocking or exciton-blocking layer in the sense of this invention is a layer which is directly adjacent to an emitting layer on the anode side. If the compounds of the formula (1) are used as hole-transport or hole-injection material, it may be preferred for them to be doped with electron-acceptor compounds, for example with $F_4$-TCNQ or with compounds as described in EP 1476881 or EP 1596445.

In still a further embodiment of the invention, the compounds of the formula (1) are employed as electron-transport material or as hole-blocking material in an electron-transport layer or hole-blocking layer. It is preferred here for $R^1$ to stand for a heteroaryl group which represents an electron-deficient heterocycle, such as, for example, imidazole, pyrazole, thiazole, benzimidazole, benzothiazole, triazole, oxadiazole, benzothiadiazole, phenanthroline, etc., or for C(=O)Ar, P(=O)Ar$_2$, S(=O)Ar or S(O)$_2$Ar, and/or for X to stand for B, P=O, P=5 or 1,3,5-triazine. It may furthermore be preferred for the compound to be doped with electron-donor compounds. A hole-blocking layer in the sense of this invention is a layer which is located between an emitting layer and an electron-transport layer and is directly adjacent to the emitting layer.

Recurring units of the formula (1) can also be employed in polymers, either as polymer backbone, as hole-transporting unit and/or as electron-trans-porting unit. The preferred substitution patterns here correspond to those described above.

Preference is furthermore given to an organic electroluminescent device, characterised in that one or more layers are applied by means of a sublimation process, in which the materials are vapour-deposited in vacuum sublimation units at an initial pressure of less than $10^{-5}$ mbar, preferably less than $10^{-6}$ mbar. However, it should be noted that the pressure may also be even lower, for example less than $10^{-7}$ mbar.

Preference is likewise given to an organic electroluminescent device, characterised in that one or more layers are applied by means of the OVPD (organic vapour phase deposition) process or with the aid of carrier-gas sublimation, in which the materials are applied at a pressure between $10^{-5}$ mbar and 1 bar. A special case of this process is the OVJP (organic vapour jet printing) process, in which the materials are applied directly through a nozzle and thus structured (for example M. S. Arnold et al., Appl. Phys. Lett. 2008, 92, 053301).

Preference is furthermore given to an organic electroluminescent device, characterised in that one or more layers are produced from solution, such as, for example, by spin coating, or by means of any desired printing process, such as, for example, screen printing, flexographic printing or offset printing, but particularly preferably LITI (light induced thermal imaging, thermal transfer printing) or ink-jet printing. Soluble compounds are necessary for this purpose. High solubility can be achieved through suitable substitution of the compounds. It is possible here to apply not only solutions of individual materials, but also solutions which comprise a plurality of compounds, for example matrix material and dopant.

It is likewise possible to apply a part of the compounds from solution and to apply a further part of the compounds by vacuum vapour deposition. Thus, for example, it is possible to apply an emitting layer from solution and to apply an electron-transport layer thereto by vapour deposition.

Finally, it should be noted that all preferred features of the above-mentioned compounds according to the invention and all features not explicitly mentioned as preferred, the use thereof in electronic devices and the electronic devices themselves can be combined with one another as desired. All resultant combinations are likewise part of this invention.

The invention will now be described in greater detail by the following examples, without wishing to restrict it thereby. The person skilled in the art will be able, without an inventive step, to synthesise further compounds according to the invention and employ them in electronic devices.

EXAMPLES

The following syntheses are carried out—unless indicated otherwise—under a protective-gas atmosphere in dried solvents. The solvents and reagents can be purchased from ALDRICH or ABCR. The precursors 2,2',2"-trisbromotriphenylamine [CAS 67242-18-6], 2,2',2",4,4',4"-hexabromotriphenylamine [CAS 5489-72-5], 2,2',2"-tribromo-4,4',4"-trimethyl-triphenylamine [CAS 32337-99-8], 4-(N-diphenylamino)phenylboronic acid [CAS 201802-67-7], 4-(N-carbazolyl)phenylboronic acid [CAS 419536-33-7] can be prepared by literature methods.

Example 1

Synthesis of 2,2',2"-tris(4-diphenylaminophenyl) triphenylamine

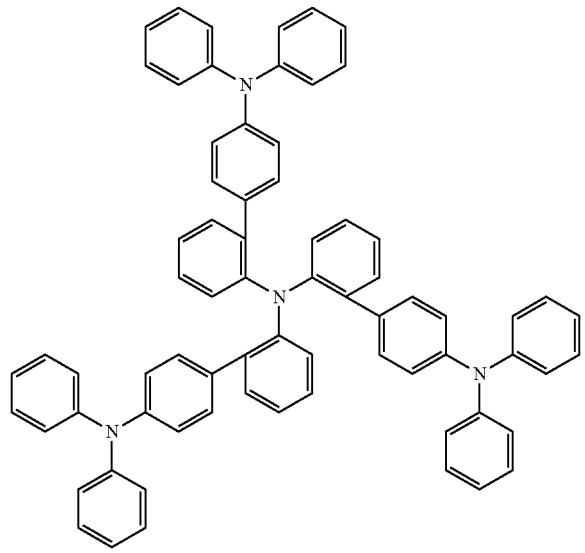 [SMILES: c1ccc(N(c2ccccc2)c2ccc(-c3ccccc3N(c3ccccc3-c3ccc(N(c4ccccc4)c4ccccc4)cc3)c3ccccc3-c3ccc(N(c4ccccc4)c4ccccc4)cc3)cc2)cc1]

5.5 g (18 mmol) of tri-o-tolylphosphine and then 674 mg (3 mmol) of palladium(II) acetate are added with vigorous stirring to a mixture of 48.2 g (100 mmol) of 2,2',2"-tribromotriphenylamine, 115.7 g (400 mmol) of 4-(N-diphenylamino)phenylboronic acid, 169.8 g (800 mmol) of tripotassium phosphate, 600 ml of toluene, 200 ml of dioxane and 800 ml of water. After the mixture has been stirred under reflux for 24 h, it is allowed to cool, the aqueous phase is separated off, and the organic phase is filtered through silica gel and evaporated to dryness. The residue is taken up in 1000 ml of dichloromethane, the solution is filtered through aluminium oxide (basic, activity grade 1), the filtrate is evaporated to dryness, and the viscous oil is taken up in about 300 ml of hot acetone. The solution is allowed to cool with stirring, and the colourless solid is filtered off with suction, washed with 50 ml of acetone and then three times with 100 ml of ethanol. After drying in vacuo and recrystallisation six times from DMF (about 6 ml/g), the solid is sublimed in vacuo (p=$10^{-5}$ mbar, T=380° C.). Yield: 53.2 g (55 mmol), 54.6%, purity 99.9% (HPLC).

The following compounds according to the invention are obtained analogously to Example 1 from corresponding amines (Examples 2-4). For Example 3, double the amount of 4-(N-diphenylamino)phenylboronic acid is employed. For Example 4, 4-(N-phenyl-1-naphthylamino)phenylboronic acid is employed instead of 4-(N-diphenylamino)phenylboronic acid.

| Ex. | Amine | Product | Yield |
|---|---|---|---|
| 2 | | | 52.4% |
| 3 | | | 47.0% |

| Ex. | Amine | Product | Yield |
|---|---|---|---|
| 4 | | | 43.5% |

Example 5

Synthesis of 2,2',2"-(tris-N-carbazolylphenyl)triphenylamine

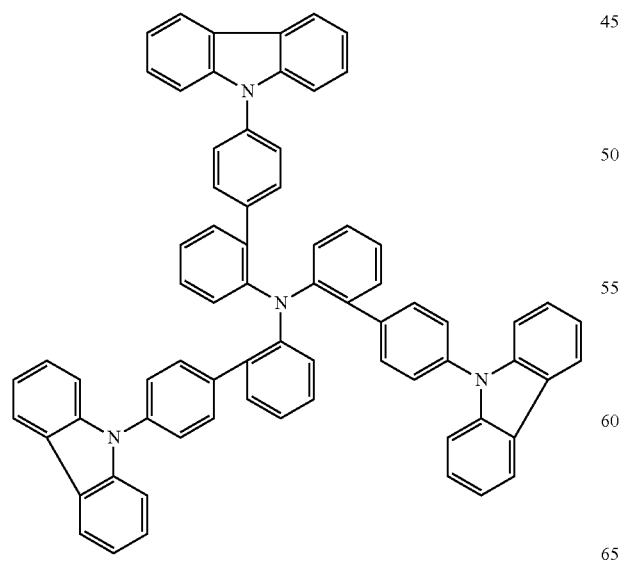

5.5 g (18 mmol) of tri-o-tolylphosphine and then 674 mg (3 mmol) of palladium(II) acetate are added with vigorous stirring to a mixture of 48.2 g (100 mmol) of 2,2',2"-tribromotriphenylamine, 114.9 g (400 mmol) of 4-(N-carbazolyl)phenylboronic acid, 169.8 g (800 mmol) of tripotassium phosphate, 600 ml of toluene, 200 ml of dioxane and 800 ml of water. After the mixture has been stirred under reflux for 24 h, it is allowed to cool, the aqueous phase is separated off, and the organic phase is filtered through silica gel and evaporated to dryness. The residue is taken up in 1000 ml of dichloromethane, the solution is filtered through aluminium oxide (basic, activity grade 1), the filtrate is evaporated to dryness, and the viscous oil is taken up in about 300 ml of hot acetone. The solution is allowed to cool with stirring, and the colourless solid is filtered off with suction, washed with 50 ml of acetone and then three times with 100 ml of ethanol. After drying in vacuo and recrystallisation five times from dioxane: EtOH (1:1, about 10 ml/g), the solid is sublimed in vacuo (p=10$^{-5}$ mbar, T=390° C.). Yield: 41.9 g (43 mmol), 43.2%, purity 99.9% (HPLC).

The following compounds according to the invention are obtained analogously to Example 5 from corresponding amines (Examples 6-7):

| Ex. | Amine | Product | Yield |
|---|---|---|---|
| 6 | | | 44.3% |
| 7 | | | 48.0% |

Example 8

Synthesis of 2,2',2"-(trisdiphenylamino)triphenylamine

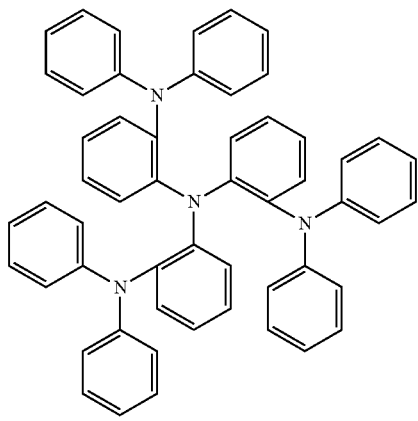 [SMILES: c1ccc(N(c2ccccc2)c2ccccc2N(c2ccccc2N(c2ccccc2)c2ccccc2)c2ccccc2N(c2ccccc2)c2ccccc2)cc1]

723 mg (4 mmol) of di-tert-butylphosphine chloride and then 674 mg (3 mmol) of palladium(II) acetate are added with vigorous stirring to a mixture of 48.2 g (100 mmol) of 2,2',2"-tribromotriphenylamine, 67.7 g (400 mmol) of diphenylamine, 57.6 g (600 mmol) of sodium tert-butoxide and 600 ml of toluene. After the mixture has been stirred under reflux for 24 h, it is allowed to cool, 1000 ml of water are added, and the organic phase is separated off, filtered through silica gel and evaporated to dryness. The residue is taken up in 1000 ml of dichloromethane, the solution is filtered through aluminium oxide (basic, activity grade 1), the filtrate is evaporated to dryness, and the viscous oil is taken up in about 300 ml of hot EtOH and a little ethyl acetate. The solution is allowed to cool with stirring, and the colourless solid is filtered off with suction and washed three times with 100 ml of ethanol. After drying in vacuo and recrystallisation five times from DMF (about 3 ml/g), the solid is sublimed in vacuo ($p=10^{-5}$ mbar, $T=365°$ C.). Yield: 25.2 g (34 mmol), 33.8%, purity 99.9% (HPLC).

The following compounds according to the invention are obtained analogously to Example 8 from corresponding amines (Examples 9 to 11).

| Ex. | Amine | Product | Yield |
|---|---|---|---|
| 11 | | | 60.1% |

Example 12
Synthesis of 2,2'-bis(diphenylamino)-2''-phenyltriphenylamine

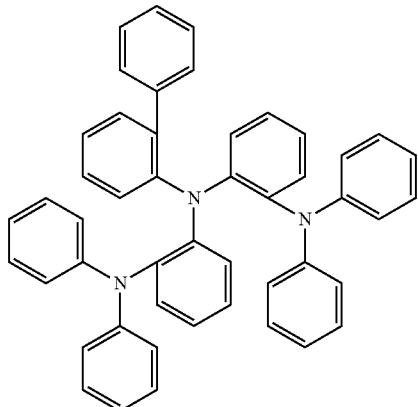

488 mg (2.7 mmol) of di-tert-butylphosphine chloride and then 449 mg (2 mmol) of palladium(II) acetate are added with vigorous stirring to a mixture of 48.2 g (100 mmol) of 2,2',2''-tribromotriphenylamine, 33.9 g (200 mmol) of diphenylamine, 28.8 g (300 mmol) of sodium tert-butoxide and 500 ml of toluene. After the mixture has been stirred under reflux for 24 h, it is allowed to cool, 1000 ml of water are added, and the organic phase is separated off, filtered through silica gel and evaporated to dryness. The viscous oil is taken up in a mixture of 400 ml of toluene and 100 ml of dioxane, 18.3 g (150 mmol) of phenylboronic acid, 42.5 g (200 mmol) of tripotassium phosphate and 500 ml of water are added, 1.83 g (6 mmol) of tri-o-tolylphosphine and 224 mg (1 mmol) of palladium(II) acetate are then added, and the mixture is heated under reflux with vigorous stirring for 16 h. After cooling, the organic phase is separated off, filtered through silica gel and evaporated to dryness. The residue is taken up in 1000 ml of dichloromethane, the solution is filtered through aluminium oxide (basic, activity grade 1), the filtrate is evaporated to dryness, and the viscous oil is taken up in about 300 ml of hot methanol and a little ethyl acetate. The solution is allowed to cool with stirring, and the beige solid is filtered off with suction and washed three times with 100 ml of ethanol. After drying in vacuo and recrystallisation five times from DMF (about 2 ml/g), the solid is sublimed in vacuo ($p=10^{-5}$ mbar, T=340° C.). Yield: 23.9 g (36 mmol), 36.5%, purity 99.9% (HPLC).

The following compounds according to the invention are obtained analogously to Example 12 from corresponding amines (Examples 13 to 15).

| Ex. | Amine | Product | Yield |
|---|---|---|---|
| 13 | | | 41.3% |

-continued

| Ex. | Amine | Product | Yield |
|---|---|---|---|
| 14 | [structure] | [structure] | 28.8% |
| 15 | [structure] | [structure] | 56.7% |

Example 16

Production and Characterisation of Organic Electroluminescent Devices which Comprise the Compounds According to the Invention Electroluminescent devices according to the invention can be produced as described, for example, in WO 05/003253. The results for various OLEDs are compared below. The basic structure, the materials used, the degree of doping and the layer thicknesses thereof are identical for better comparability.

The first device example describes a comparative standard in accordance with the prior art, in which the emission layer consists of the host material spiro-ketone and the guest material (dopant) Ir(ppy)₃. Furthermore, OLEDs having various structures are described, each with the guest material (dopant) Ir(ppy)₃. OLEDs having the following structure are produced analogously to the general process mentioned above:

| | |
|---|---|
| hole-injection layer (HIL) | 20 nm of 2,2',7,7'-tetrakis(di-para-tolyl-amino)spiro-9,9'-bifluorene |
| hole-transport layer 1 (HTL-1) | 20 nm of NPB (N-naphthyl-N-phenyl-4,4'-diaminobiphenyl) |
| hole-transport layer 2 (HTL-2) | 10 nm of compound according to the invention from Ex. 1 |
| emission layer (EML) | 40 nm of host: spiro-ketone (SK) (bis(9,9'-spirobifluoren-2-yl) ketone) as comparison Dopant: Ir(ppy)₃ (10% by vol. doping, vapour-deposited, synthesised in accordance with WO 03/0068526) |
| or | |
| emission layer (EML) | 40 nm of host: 55% by vol. of spiro-ketone (SK) (bis(9,9'-spirobifluoren-2-yl) ketone) and 35% by vol. of the compound according to the invention from Ex. 5 in a mixture Dopant: Ir(ppy)₃ (10% by vol. doping, applied by vapour deposition, synthesised in accordance with WO 03/0068526) |
| electron conductor (ETL) | 20 nm of AlQ₃ (tris(quinolinato)aluminium(III)) |
| cathode | 1 nm of LiF, 150 nm of Al on top. |

The structures of Ir(ppy)₃ and spiro-ketone are depicted below for clarity:

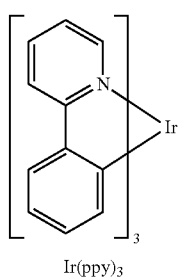

Ir(ppy)₃

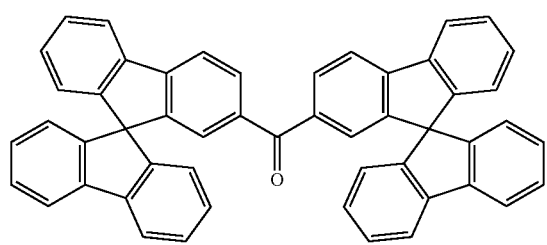

Spiro-ketone (SK)

The compounds of Examples 1, 2 and 5 are depicted again below:

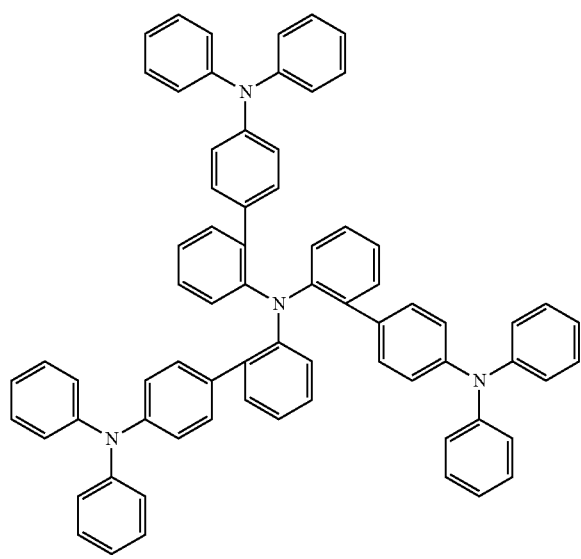

Compound from Ex. 1

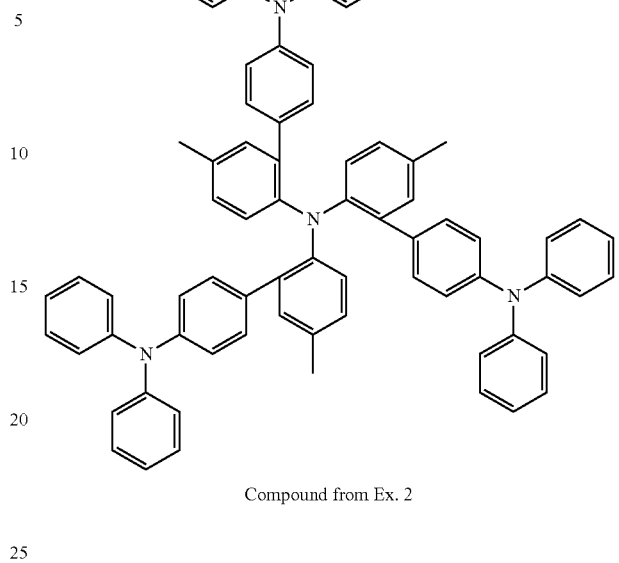

Compound from Ex. 2

Compound from Ex. 5

These as yet unoptimised OLEDs are characterised by standard methods; for this purpose, the electroluminescence spectra, the efficiency (measured in cd/A) as a function of the luminance, calculated from current/voltage/luminance characteristic lines (IUL characteristic lines), and the lifetime are determined.

Table 1 shows the results of the device characterisation. The devices comprising the compounds according to the invention exhibit a comparable lifetime or a considerably improved lifetime in the mixed-host system (Examples 19 and 20) at the same time as significantly improved efficiency.

TABLE 1

Device results with compounds according to the invention with Ir(ppy)₃ as dopant

| Ex. | HTL-2 | EML | Max. eff. [cd/A] | Voltage at 1000 cd/m² | CIE (x, y) | Lifetime [h], initial luminance 1000 cd/m² |
|---|---|---|---|---|---|---|
| 17 (comp.) | none | 90% of SK 10% of Ir(ppy)₃ | 30 | 4.4 | 0.38/0.57 | 7700 |
| 18 | Ex. 1 | 90% of SK 10% of Ir(ppy)₃ | 51 | 4.5 | 0.38/0.58 | 7000 |
| 19 | Ex. 2 | 90% of SK 10% of Ir(ppy)₃ | 48 | 4.3 | 0.38/0.58 | 6900 |
| 20 | none | 55% of SK 35% of Ex. 5 10% of Ir(ppy)₃ | 35 | 4.1 | 0.31/0.60 | 11000 |
| 21 | Ex. 1 | 55% of SK 35% of Ex. 5 10% of Ir(ppy)₃ | 54 | 4.0 | 0.37/0.59 | 17000 |

The invention claimed is:

1. A compound of formula (1)

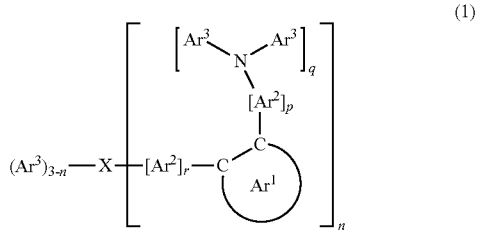

wherein

X is on each occurrence, identically or differently, N, B, P, P=O, P=S, 1,3,5-triazine, N(Ar²)₃;

Ar¹ is on each occurrence, identically or differently, a group which, together with the group C—C, forms an aryl or heteroaryl group having 5 to 30 aromatic ring atoms optionally substituted by one or more radicals R¹;

Ar² is on each occurrence, identically or differently, a divalent aryl or heteroaryl group having 5 to 30 aromatic ring atoms, in each case optionally substituted by one or more radicals R¹; and wherein two radicals Ar² which are bonded to the same group X are optionally linked to one another by a single bond or a bridge selected from B(R²), C(R²)₂, Si(R²)₂, C=O, C=NR², C=C(R²)₂, O, S, S=O, SO₂, N(R²), P(R²) and P(=O)R²;

Ar³ is on each occurrence, identically or differently, an aromatic or heteroaromatic ring system having 5 to 10 C atoms, which in each case is optionally substituted by one or more radicals R¹; and wherein two radicals Ar³ which are bonded to the same N are optionally linked to one another by a single bond or a bridge selected from B(R²), C(R²)₂, Si(R²)₂, C=O, C=NR², C=C(R²)₂, O, S, S=O, SO₂, N(R²), P(R²) and P(=O)R²;

R¹ is on each occurrence, identically or differently, H, D, F, Cl, Br, I, CHO, C(=O)Ar, P(=O)(Ar)₂, S(=O)Ar, S(=O)₂Ar, CR²=CR²Ar, CN, NO₂, Si(R²)₃, B(OR²)₂, B(R²)₂, B(N(R²)₂)₂, OSO₂R², a straight-chain alkyl, alkoxy or thioalkoxy group having 1 to 40 C atoms or a branched or cyclic alkyl, alkoxy or thioalkoxy group having 3 to 40 C atoms or an alkenyl or alkynyl group having 2 to 40 C atoms, each of which are optionally substituted by one or more radicals R², where one or more non-adjacent CH₂ groups are optionally replaced by R²C=CR², C≡C, Si(R²)₂, Ge(R²)₂, Sn(R²)₂, C=O, C=S, C=Se, C=NR², P(=O)(R²), SO, SO₂, NR², O, S or CONR² and where one or more H atoms are optionally replaced by D, F, Cl, Br, I, CN or NO₂, or an aromatic or heteroaromatic ring system having 5 to 60 aromatic ring atoms, which in each case is optionally substituted by one or more radicals R², or an aryloxy or heteroaryloxy group having 5 to 60 aromatic ring atoms, which in each case is optionally substituted by one or more radicals R², or a combination of these systems; and wherein two or more adjacent substituents R¹ optionally define a mono- or polycyclic, aliphatic or aromatic ring system with one another;

Ar is on each occurrence, identically or differently, an aromatic or heteroaromatic ring system having 5 to 30 aromatic ring atoms, optionally substituted by one or more non-aromatic radicals R¹;

R² is on each occurrence, identically or differently, H, D or an aliphatic, aromatic and/or heteroaromatic organic radical having 1 to 20 C atoms, in which H atoms are optionally replaced by D or F; and wherein two or more adjacent substituents R² here optionally define a mono- or polycyclic, aliphatic or aromatic ring system with one another;

n is 2 or 3;

P is on each occurrence, identically or differently, 0, 1 or 2;

q is 1 if p=0, 1 or 2 if p=1, and 1 or 2 if p=2;

r is on each occurrence, identically or differently, 0, 1 or 2.

2. The compound of claim 1, wherein said compound is a compound of formula (2), (3) or (4):

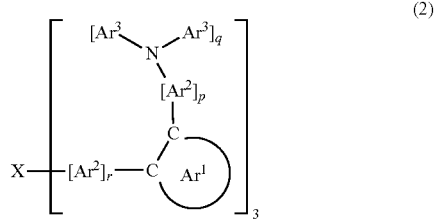

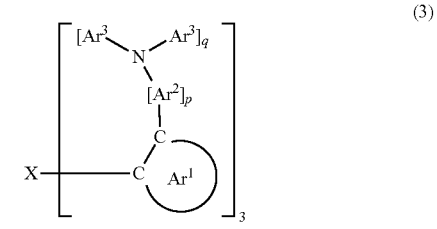

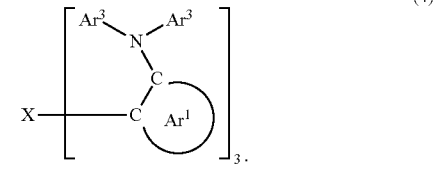

3. The compound of claim 1, wherein X is N, N(Ar²)₃, P=O, or 1,3,5-triazine.

4. The compound of claim 1, wherein Ar¹ is benzene, optionally substituted by one or more substituents R¹.

5. The compound of claim 4, wherein $Ar^1$ is benzene, which is substituted by a substituent $R^1$ which is not equal to H or D in the para-position to X.

6. The compound of claim 1, wherein $Ar^2$ is naphthalene or benzene, each of which may be substituted by one or more radicals $R^1$.

7. The compound of claim 1, wherein $Ar^3$ is thiophene, phenyl or naphthalene, each of which may be substituted by one or more radicals $R^1$; a plurality of radicals $Ar^1$ here may also be linked to one another by a single bond or a divalent group, as described in claim 1.

8. The compound of claim 1, wherein $R^1$ is H, D, CN, F, Br, I, a straight-chain alkyl group having 1 to 6 C atoms or a branched or cyclic alkyl group having 3 to 6 C atoms, each of which may be substituted by one or more non-aromatic radicals $R^2$, where one or more H atoms may be replaced by D or F, or an aromatic or heteroaromatic ring system having 5 to 18 aromatic ring atoms, which may be substituted by one or more non-aromatic radicals $R^2$.

9. Dimers, trimers, tetramers, pentamers, oligomers, polymers or dendrimers comprising one or more compounds according to claim 1, where one or more radicals $R^1$ or $R^2$ represent bonds between the compounds of the formula (1) in the dimer, trimer, tetramer or pentamer or bonds from the compounds of the formula (1) to the polymer, oligomer or dendrimer.

10. Mixture comprising at least one compound according to claim 1 and at least one further compound.

11. Formulation comprising at least one compound according to claim 1 or a mixture according to claim 10 and at least one solvent.

12. Process for the preparation of compounds according to claim 1, characterised in that either the group $(Ar^3)_2N$—$Ar^2$ is introduced as boronic acid derivative in a Suzuki coupling or the group $(Ar^3)_2N$ is introduced as $(Ar^3)_2NH$ in a Hartwig-Buchwald coupling.

13. An electronic device comprising at least one compound according to claim 1.

14. The electronic device according to claim 13, wherein the compound according to claim 1 is employed as matrix material for fluorescent or phosphorescent compounds and/or in that the compound according to claim 1 is employed as hole-transport material or as hole-injection material or as electron-blocking material or as exciton-blocking material and/or in that the compound according to claim 1 is employed as electron-transport material or as hole-blocking material.

15. A compound of claim 1, wherein said compound is a compound of formula (5)

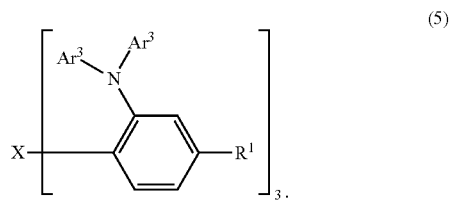

16. An electronic device comprising at least one mixture according to claim 10.

17. The electronic device of claim 13, wherein said device is an organic electroluminescent device (OLED), an organic field-effect transistor (O-FET), an organic thin-film transistor (O-TFT), an organic light-emitting transistor (O-LET), an organic integrated circuit (O-IC), an organic solar cell (O-SC), an organic field-quench device (O-FQD), a light-emitting electrochemical cell (LEC), an organic laser diode (O-laser) or an organic photoreceptor.

18. The electronic device of claim 16, wherein said device is an organic electroluminescent device (OLED), an organic field-effect transistor (O-FET), an organic thin-film transistor (O-TFT), an organic light-emitting transistor (O-LET), an organic integrated circuit (O-IC), an organic solar cell (O-SC), an organic field-quench device (O-FQD), a light-emitting electrochemical cell (LEC), an organic laser diode (G-laser) or an organic photoreceptor.

* * * * *